United States Patent
Bhattacharya et al.

(10) Patent No.: US 11,324,954 B2
(45) Date of Patent: May 10, 2022

(54) ACHIEVING SMOOTH BREATHING BY MODIFIED BILATERAL PHRENIC NERVE PACING

(71) Applicant: Covidien LP, Mansfield, MA (US)

(72) Inventors: Abhijit Bhattacharya, Hyderabad (IN); Berthold Stegemann, Kassel (DE)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/888,960

(22) Filed: Jun. 1, 2020

(65) Prior Publication Data

US 2020/0406034 A1    Dec. 31, 2020

Related U.S. Application Data

(60) Provisional application No. 62/868,280, filed on Jun. 28, 2019.

(51) Int. Cl.
*A61N 1/36* (2006.01)

(52) U.S. Cl.
CPC ........ *A61N 1/3611* (2013.01); *A61N 1/36139* (2013.01); *A61N 1/36153* (2013.01); *A61N 1/36192* (2013.01)

(58) Field of Classification Search
CPC .............................. A61N 1/3601; A61N 1/3611
See application file for complete search history.

(56) References Cited

U.S. PATENT DOCUMENTS

| | | |
|---|---|---|
| 1,202,125 A | 10/1916 | Tullar |
| 1,202,126 A | 10/1916 | Tullar |
| 1,241,056 A | 9/1917 | Tullar |
| 2,914,067 A | 11/1959 | Meidenbauer |
| 3,339,545 A | 9/1967 | Barnett |
| 3,584,618 A | 6/1971 | Reinhard et al. |
| 3,584,621 A | 6/1971 | Bird et al. |
| 3,586,021 A | 6/1971 | McGuinness |
| 3,628,531 A | 12/1971 | Harris |
| 3,633,576 A | 1/1972 | Gorsuch |
| 3,643,652 A | 2/1972 | Beltran |

(Continued)

FOREIGN PATENT DOCUMENTS

| | | |
|---|---|---|
| AU | 142112 | 9/1996 |
| CA | 2036184 | 11/1991 |

(Continued)

OTHER PUBLICATIONS

Luo, Y. M. et al., "Diaphragm ENG measured by cervical magnetic and electrical phrenic nerve stimulation", J Appl Physiol (1985), Dec. 1998; 85;(6), 2089-2099.

(Continued)

*Primary Examiner* — Allen Porter

(57) ABSTRACT

A system for stimulating phrenic nerves to provide smooth breathing patterns is provided. More specifically, by identifying contraction threshold voltages for muscles associated with each of the left and right portions of a patient's diaphragm, a phrenic nerve pacing signal customized for each phrenic nerve may be provided to a patient. More specifically, a voltage of a pacing voltage provided to a first phrenic nerve may be less than the contraction threshold while a voltage of a pacing voltage provided to a second phrenic nerve may be greater than the contraction threshold.

20 Claims, 9 Drawing Sheets

(56) References Cited

U.S. PATENT DOCUMENTS

| | | |
|---|---|---|
| 3,662,751 A | 5/1972 | Barkalow et al. |
| 3,664,370 A | 5/1972 | Warnow |
| 3,669,108 A | 6/1972 | Sundblom et al. |
| 3,695,263 A | 10/1972 | Kipling |
| 3,722,510 A | 3/1973 | Parker |
| 3,739,776 A | 6/1973 | Bird et al. |
| 3,741,208 A | 6/1973 | Jonsson et al. |
| 3,753,436 A | 8/1973 | Bird et al. |
| 3,756,229 A | 9/1973 | Ollivier |
| 3,759,249 A | 9/1973 | Fletcher et al. |
| 3,768,468 A | 10/1973 | Cox |
| 3,789,837 A | 2/1974 | Philips et al. |
| 3,834,382 A | 9/1974 | Lederman et al. |
| 3,889,669 A | 6/1975 | Weigl |
| 3,896,800 A | 7/1975 | Cibulka |
| 3,903,881 A | 9/1975 | Weigl |
| 3,905,362 A | 9/1975 | Eyrick et al. |
| 3,910,261 A | 10/1975 | Ragsdale et al. |
| 3,911,899 A | 10/1975 | Hattes |
| 3,952,739 A | 4/1976 | Cibulka |
| 3,957,044 A | 5/1976 | Fletcher et al. |
| 3,961,627 A | 6/1976 | Ernst et al. |
| 3,968,794 A | 7/1976 | O'Neill |
| 3,968,795 A | 7/1976 | O'Neill et al. |
| 3,976,052 A | 8/1976 | Junginger et al. |
| 3,981,301 A | 9/1976 | Warnow et al. |
| 3,985,131 A | 10/1976 | Buck et al. |
| 3,991,304 A | 11/1976 | Hillsman |
| 4,003,377 A | 1/1977 | Dahl |
| 4,029,120 A | 6/1977 | Christianson |
| 4,044,763 A | 8/1977 | Bird |
| 4,050,458 A | 9/1977 | Friend |
| 4,060,078 A | 11/1977 | Bird |
| 4,121,578 A | 10/1978 | Torzala |
| 4,155,357 A | 5/1979 | Dahl |
| 4,164,219 A | 8/1979 | Bird |
| 4,197,856 A | 4/1980 | Northrop |
| 4,211,221 A | 7/1980 | Schwanbom et al. |
| 4,258,718 A | 3/1981 | Goldman |
| 4,275,722 A | 6/1981 | Sorensen |
| 4,281,651 A | 8/1981 | Cox |
| 4,284,075 A | 8/1981 | Krasberg |
| 4,294,242 A | 10/1981 | Cowans |
| 4,299,236 A | 11/1981 | Poirier |
| 4,316,182 A | 2/1982 | Hodgson |
| 4,323,064 A | 4/1982 | Hoenig et al. |
| 4,340,044 A | 7/1982 | Levy et al. |
| 4,351,344 A | 9/1982 | Stenzler |
| 4,366,821 A | 1/1983 | Wittmaier et al. |
| 4,401,115 A | 8/1983 | Monnier |
| 4,433,693 A | 2/1984 | Hochstein |
| 4,440,166 A | 4/1984 | Winkler et al. |
| 4,442,835 A | 4/1984 | Carnegie |
| 4,448,192 A | 5/1984 | Stawitcke et al. |
| 4,459,982 A | 7/1984 | Fry |
| 4,459,983 A | 7/1984 | Beyreuther et al. |
| 4,498,471 A | 2/1985 | Kranz et al. |
| 4,503,850 A | 3/1985 | Pasternak |
| 4,506,667 A | 3/1985 | Ansite |
| 4,522,639 A | 6/1985 | Ansite et al. |
| 4,539,984 A | 9/1985 | Kiszel et al. |
| 4,550,726 A | 11/1985 | McEwen |
| 4,554,916 A | 11/1985 | Watt |
| 4,558,710 A | 12/1985 | Eichler |
| 4,566,450 A | 1/1986 | Brossman, Jr. |
| 4,598,706 A | 7/1986 | Darowski et al. |
| 4,606,340 A | 8/1986 | Ansite |
| 4,612,928 A | 9/1986 | Tiep et al. |
| 4,630,605 A | 12/1986 | Pasternack |
| 4,640,277 A | 2/1987 | Meyer et al. |
| 4,648,407 A | 3/1987 | Sackner |
| 4,653,493 A | 3/1987 | Hoppough |
| 4,757,824 A | 7/1988 | Chaumet |
| 4,766,894 A | 8/1988 | Legrand et al. |
| 4,796,618 A | 1/1989 | Garraffa |
| 4,870,960 A | 10/1989 | Hradek |
| 4,889,116 A | 12/1989 | Taube |
| 4,981,295 A | 1/1991 | Belman et al. |
| 4,982,735 A | 1/1991 | Yagata et al. |
| 4,984,158 A | 1/1991 | Hillsman |
| 4,990,894 A | 2/1991 | Loescher et al. |
| 5,007,420 A | 4/1991 | Bird |
| 5,016,626 A | 5/1991 | Jones |
| 5,022,393 A | 6/1991 | McGrady et al. |
| 5,048,515 A | 9/1991 | Sanso |
| 5,072,737 A | 12/1991 | Goulding |
| 5,099,837 A | 3/1992 | Russel, Sr. et al. |
| 5,107,830 A | 4/1992 | Younes |
| 5,107,831 A | 4/1992 | Halpern et al. |
| 5,154,167 A | 10/1992 | Hepburn |
| 5,156,145 A | 10/1992 | Flood et al. |
| 5,161,525 A | 11/1992 | Kimm et al. |
| 5,165,397 A | 11/1992 | Arp |
| 5,273,031 A | 12/1993 | Olsson et al. |
| 5,293,875 A | 3/1994 | Stone |
| 5,307,795 A | 5/1994 | Whitwam et al. |
| 5,316,009 A | 5/1994 | Yamada |
| 5,318,487 A | 6/1994 | Golen et al. |
| 5,322,059 A | 6/1994 | Walther |
| 5,323,772 A | 6/1994 | Linden et al. |
| 5,335,654 A | 8/1994 | Rapoport |
| 5,355,893 A | 10/1994 | Mick et al. |
| 5,373,842 A | 12/1994 | Olsson et al. |
| 5,385,142 A | 1/1995 | Brady et al. |
| 5,390,666 A | 2/1995 | Kimm et al. |
| 5,398,682 A | 3/1995 | Lynn |
| 5,404,871 A | 4/1995 | Goodman et al. |
| 5,429,123 A | 7/1995 | Shaffer et al. |
| 5,433,193 A | 7/1995 | Sanders et al. |
| 5,458,137 A | 10/1995 | Axe et al. |
| 5,477,860 A | 12/1995 | Essen Moller |
| 5,479,920 A | 1/1996 | Piper et al. |
| 5,485,833 A | 1/1996 | Dietz |
| 5,487,383 A | 1/1996 | Levinson |
| 5,494,028 A | 2/1996 | DeVries et al. |
| 5,524,616 A | 6/1996 | Smith et al. |
| RE35,295 E | 7/1996 | Estes et al. |
| 5,533,512 A | 7/1996 | Novotny et al. |
| 5,535,738 A | 7/1996 | Estes et al. |
| 5,540,218 A | 7/1996 | Jones et al. |
| 5,540,220 A | 7/1996 | Gropper et al. |
| 5,549,655 A | 8/1996 | Erickson |
| 5,551,419 A | 9/1996 | Froehlich et al. |
| 5,564,416 A | 10/1996 | Jones |
| 5,579,774 A | 12/1996 | Miller et al. |
| 5,582,163 A | 12/1996 | Bonassa |
| 5,582,182 A | 12/1996 | Hillsman |
| 5,596,984 A | 1/1997 | O'Mahony et al. |
| 5,603,315 A | 2/1997 | Sasso, Jr. |
| 5,605,151 A | 2/1997 | Lynn |
| 5,608,647 A | 3/1997 | Rubsamen et al. |
| 5,632,269 A | 5/1997 | Zdrojkowski |
| 5,632,281 A | 5/1997 | Rayburn |
| 5,645,053 A | 7/1997 | Remmers et al. |
| 5,647,345 A | 7/1997 | Saul |
| 5,647,351 A | 7/1997 | Weismann et al. |
| 5,660,171 A | 8/1997 | Kimm et al. |
| 5,662,099 A | 9/1997 | Tobia et al. |
| 5,664,560 A | 9/1997 | Merrick et al. |
| 5,685,318 A | 11/1997 | Elghazzawi |
| 5,692,497 A | 12/1997 | Schnitzer et al. |
| 5,706,799 A | 1/1998 | Imai et al. |
| 5,720,277 A | 2/1998 | Olsson et al. |
| 5,727,562 A | 3/1998 | Beck |
| 5,730,121 A | 3/1998 | Hawkins, Jr. et al. |
| 5,735,267 A | 4/1998 | Tobia |
| 5,738,090 A | 4/1998 | Lachmann et al. |
| 5,740,796 A | 4/1998 | Skog |
| 5,752,509 A | 5/1998 | Lachmann et al. |
| 5,794,615 A | 8/1998 | Estes |
| 5,797,393 A | 8/1998 | Kohl |
| 5,800,361 A | 9/1998 | Rayburn |
| 5,803,065 A | 9/1998 | Zdrojkowski et al. |
| 5,803,066 A | 9/1998 | Rapoport et al. |

(56) References Cited

U.S. PATENT DOCUMENTS

| | | |
|---|---|---|
| 5,810,741 A | 9/1998 | Essen Moller |
| 5,832,916 A | 11/1998 | Lundberg |
| 5,832,919 A | 11/1998 | Kano et al. |
| 5,836,300 A | 11/1998 | Mault |
| 5,857,460 A | 1/1999 | Popitz |
| 5,860,418 A | 1/1999 | Lundberg |
| 5,865,173 A | 2/1999 | Froehlich |
| 5,876,353 A | 3/1999 | Riff |
| 5,891,023 A | 4/1999 | Lynn |
| 5,909,731 A | 6/1999 | O'Mahony et al. |
| 5,915,381 A | 6/1999 | Nord |
| 5,921,238 A | 7/1999 | Bourdon |
| 5,927,274 A | 7/1999 | Servidio et al. |
| 5,931,160 A | 8/1999 | Gilmore et al. |
| 5,931,162 A | 8/1999 | Christian |
| 5,934,274 A | 8/1999 | Merrick et al. |
| 5,957,129 A | 9/1999 | Tham et al. |
| 5,964,218 A | 10/1999 | Smith et al. |
| 5,996,580 A | 12/1999 | Swann |
| 6,029,660 A | 2/2000 | Calluaud et al. |
| 6,041,780 A | 3/2000 | Richard et al. |
| 6,044,841 A | 4/2000 | Verdun et al. |
| 6,066,101 A | 5/2000 | Johnson et al. |
| 6,076,519 A | 6/2000 | Johnson |
| 6,095,140 A | 8/2000 | Poon et al. |
| 6,099,481 A | 8/2000 | Daniels et al. |
| 6,109,259 A | 8/2000 | Fitzgerald |
| 6,112,744 A | 9/2000 | Hognelid |
| 6,116,240 A | 9/2000 | Merrick et al. |
| 6,123,072 A | 9/2000 | Downs |
| 6,135,105 A | 10/2000 | Lampotang et al. |
| 6,135,107 A | 10/2000 | Mault |
| 6,138,675 A | 10/2000 | Berthon-Jones |
| 6,139,506 A | 10/2000 | Heinonen |
| 6,142,150 A | 11/2000 | O'Mahoney |
| 6,148,814 A | 11/2000 | Clemmer et al. |
| 6,158,432 A | 12/2000 | Biondi et al. |
| 6,158,433 A | 12/2000 | Ong et al. |
| 6,161,539 A | 12/2000 | Winter |
| 6,168,568 B1 | 1/2001 | Gavriely |
| 6,179,784 B1 | 1/2001 | Daniels et al. |
| 6,200,271 B1 | 3/2001 | Kuck et al. |
| 6,210,342 B1 | 4/2001 | Kuck et al. |
| 6,213,120 B1 | 4/2001 | Block et al. |
| 6,216,690 B1 | 4/2001 | Keitel et al. |
| 6,220,244 B1 | 4/2001 | McLaughlin |
| 6,223,064 B1 | 4/2001 | Lynn et al. |
| 6,227,197 B1 | 5/2001 | Fitzgerald |
| 6,230,708 B1 | 5/2001 | Radko |
| 6,238,351 B1 | 5/2001 | Orr et al. |
| 6,253,765 B1 | 7/2001 | Hognelid et al. |
| 6,258,038 B1 | 7/2001 | Haryadi et al. |
| 6,258,039 B1 | 7/2001 | Okamoto et al. |
| 6,273,088 B1 | 8/2001 | Hillsman |
| 6,279,576 B1 | 8/2001 | Lambert |
| 6,305,374 B1 | 10/2001 | Zdrojkowski et al. |
| 6,309,360 B1 | 10/2001 | Mault |
| 6,312,389 B1 | 11/2001 | Kofoed et al. |
| 6,318,365 B1 | 11/2001 | Vogele et al. |
| 6,341,604 B1 | 1/2002 | Kellon |
| 6,342,039 B1 | 1/2002 | Lynn et al. |
| 6,345,619 B1 | 2/2002 | Finn |
| 6,397,838 B1 | 6/2002 | Zimlich, Jr. et al. |
| 6,399,799 B1 | 6/2002 | Pereira et al. |
| 6,415,183 B1 | 7/2002 | Scheiner |
| 6,439,229 B1 | 8/2002 | Du et al. |
| 6,439,234 B1 | 8/2002 | Curti et al. |
| 6,446,630 B1 | 9/2002 | Todd, Jr. |
| 6,450,163 B1 | 9/2002 | Blacker et al. |
| 6,457,472 B1 | 10/2002 | Schwartz et al. |
| 6,463,930 B2 | 10/2002 | Biondi et al. |
| 6,467,477 B1 | 10/2002 | Frank et al. |
| 6,467,478 B1 | 10/2002 | Merrick et al. |
| 6,467,481 B1 | 10/2002 | Eswarappa |
| 6,471,658 B1 | 10/2002 | Daniels et al. |
| 6,484,719 B1 | 11/2002 | Berthon-Jones |
| 6,512,938 B2 | 1/2003 | Claure et al. |
| 6,526,970 B2 | 3/2003 | DeVries et al. |
| 6,526,974 B1 | 3/2003 | Brydon et al. |
| 6,532,957 B2 | 3/2003 | Berthon-Jones |
| 6,532,959 B1 | 3/2003 | Berthon-Jones |
| 6,533,730 B2 | 3/2003 | Stroem |
| 6,536,433 B1 | 3/2003 | Cewers |
| 6,537,228 B1 | 3/2003 | Lambert |
| 6,539,940 B2 | 4/2003 | Zdrojkowski et al. |
| 6,540,689 B1 | 4/2003 | Orr et al. |
| 6,553,992 B1 | 4/2003 | Berthon-Jones et al. |
| 6,575,163 B1 | 6/2003 | Berthon-Jones |
| 6,575,164 B1 | 6/2003 | Jaffe et al. |
| 6,575,918 B2 | 6/2003 | Kline |
| 6,577,884 B1 | 6/2003 | Boas |
| 6,581,597 B2 | 6/2003 | Sugiura |
| 6,588,423 B1 | 7/2003 | Sinderby |
| 6,595,212 B1 | 7/2003 | Arnott |
| 6,601,583 B2 | 8/2003 | Pessala et al. |
| 6,607,481 B1 | 8/2003 | Clawson |
| 6,609,016 B1 | 8/2003 | Lynn |
| 6,616,615 B2 | 9/2003 | Mault |
| 6,619,289 B1 | 9/2003 | Mashak |
| 6,622,725 B1 | 9/2003 | Fisher et al. |
| 6,622,726 B1 | 9/2003 | Du |
| 6,626,175 B2 | 9/2003 | Jafari et al. |
| 6,629,933 B1 | 10/2003 | Lindner |
| 6,629,934 B2 | 10/2003 | Mault et al. |
| 6,648,831 B2 | 11/2003 | Orr et al. |
| 6,648,832 B2 | 11/2003 | Orr et al. |
| 6,655,383 B1 | 12/2003 | Lundberg |
| 6,655,385 B1 | 12/2003 | Curti et al. |
| 6,668,824 B1 | 12/2003 | Isaza et al. |
| 6,668,829 B2 | 12/2003 | Biondi et al. |
| 6,671,529 B2 | 12/2003 | Claure et al. |
| 6,679,258 B1 | 1/2004 | Ström |
| 6,688,307 B2 | 2/2004 | Berthon-Jones |
| 6,694,978 B1 | 2/2004 | Bennarsten |
| 6,722,360 B2 | 4/2004 | Doshi |
| 6,748,252 B2 | 6/2004 | Lynn et al. |
| 6,758,216 B1 | 7/2004 | Berthon-Jones et al. |
| 6,760,608 B2 | 7/2004 | Lynn |
| 6,763,829 B2 | 7/2004 | Jaffe et al. |
| 6,810,876 B2 | 11/2004 | Berthon-Jones |
| 6,823,866 B2 | 11/2004 | Jafari et al. |
| 6,837,241 B2 | 1/2005 | Samzelius |
| 6,860,266 B2 | 3/2005 | Blike |
| 6,863,068 B2 | 3/2005 | Jamison et al. |
| 6,863,656 B2 | 3/2005 | Lurie |
| 6,866,040 B1 | 3/2005 | Bourdon |
| 6,881,193 B2 | 4/2005 | Kline |
| 6,884,222 B1 | 4/2005 | Braig |
| 6,899,101 B2 | 5/2005 | Haston et al. |
| 6,920,875 B1 | 7/2005 | Hill et al. |
| 6,920,878 B2 | 7/2005 | Sinderby et al. |
| 6,935,336 B2 | 8/2005 | Lurie et al. |
| 6,938,618 B2 | 9/2005 | Lurie et al. |
| 6,938,619 B1 | 9/2005 | Hickle |
| 6,948,497 B2 | 9/2005 | Zdrojkowski et al. |
| 6,949,075 B2 | 9/2005 | Hatlesad et al. |
| 6,949,133 B2 | 9/2005 | McCombs et al. |
| 6,955,651 B2 | 10/2005 | Kück et al. |
| 6,988,498 B2 | 1/2006 | Berthon-Jones et al. |
| 6,990,977 B1 | 1/2006 | Calluaud et al. |
| 6,990,980 B2 | 1/2006 | Richey, II |
| 6,997,880 B2 | 2/2006 | Carlebach et al. |
| 7,000,612 B2 | 2/2006 | Jafari et al. |
| 7,008,380 B1 | 3/2006 | Rees et al. |
| 7,011,091 B2 | 3/2006 | Hill et al. |
| 7,011,092 B2 | 3/2006 | McCombs et al. |
| 7,017,574 B2 | 3/2006 | Biondi et al. |
| 7,018,340 B2 | 3/2006 | Jaffe et al. |
| 7,024,235 B2 | 4/2006 | Melker et al. |
| 7,025,731 B2 | 4/2006 | Orr et al. |
| 7,040,320 B2 | 5/2006 | Fjeld et al. |
| 7,040,321 B2 | 5/2006 | Gobel |
| 7,047,071 B2 | 5/2006 | Wagner et al. |
| 7,066,175 B2 | 6/2006 | Hamilton et al. |

(56) References Cited

U.S. PATENT DOCUMENTS

| | | |
|---|---|---|
| 7,066,176 B2 | 6/2006 | Jaffe et al. |
| 7,066,892 B2 | 6/2006 | Kline |
| 7,070,566 B2 | 7/2006 | Medero et al. |
| 7,070,569 B2 | 7/2006 | Heinonen et al. |
| 7,070,570 B2 | 7/2006 | Sanderson et al. |
| 7,074,196 B2 | 7/2006 | Kück et al. |
| 7,077,132 B2 | 7/2006 | Berthon-Jones |
| 7,080,646 B2 | 7/2006 | Wiesmann et al. |
| 7,081,095 B2 | 7/2006 | Lynn et al. |
| 7,083,574 B2 | 8/2006 | Kline |
| 7,087,027 B2 | 8/2006 | Page |
| 7,089,930 B2 | 8/2006 | Adams et al. |
| 7,089,932 B2 | 8/2006 | Dodds |
| 7,100,607 B2 | 9/2006 | Zdrojkowski et al. |
| 7,100,609 B2 | 9/2006 | Berthon-Jones et al. |
| 7,104,962 B2 | 9/2006 | Lomask et al. |
| 7,104,964 B2 | 9/2006 | Kline |
| 7,108,666 B2 | 9/2006 | Stenzler |
| 7,117,035 B2 | 10/2006 | Wagner et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,152,604 B2 | 12/2006 | Hickle et al. |
| 7,185,649 B2 | 3/2007 | Lurie |
| 7,195,012 B2 | 3/2007 | Lurie |
| 7,207,947 B2 | 4/2007 | Koh et al. |
| 7,210,480 B2 | 5/2007 | Lurie et al. |
| 7,211,049 B2 | 5/2007 | Bradley et al. |
| 7,218,966 B2 | 5/2007 | Haefner |
| 7,225,022 B2 | 5/2007 | Anderson et al. |
| 7,236,819 B2 | 6/2007 | Brockway et al. |
| 7,267,652 B2 | 9/2007 | Coyle et al. |
| 7,273,050 B2 | 9/2007 | Wei |
| 7,275,540 B2 | 10/2007 | Bolam et al. |
| 7,275,542 B2 | 10/2007 | Lurie et al. |
| 7,276,031 B2 | 10/2007 | Norman et al. |
| 7,302,294 B2 | 11/2007 | Kamath et al. |
| 7,302,295 B2 | 11/2007 | Stahmann et al. |
| 7,311,668 B2 | 12/2007 | Lurie |
| 7,320,321 B2 | 1/2008 | Pranger et al. |
| 7,334,578 B2 | 2/2008 | Biondi et al. |
| 7,336,996 B2 | 2/2008 | Hartley et al. |
| 7,344,497 B2 | 3/2008 | Kline |
| 7,347,204 B1 | 3/2008 | Lindsey et al. |
| 7,349,742 B2 | 3/2008 | Heil et al. |
| 7,364,547 B2 | 4/2008 | Stahmann et al. |
| 7,367,337 B2 | 5/2008 | Berthon-Jones et al. |
| 7,389,138 B2 | 6/2008 | Wagner et al. |
| 7,390,304 B2 | 6/2008 | Chen et al. |
| 7,392,806 B2 | 7/2008 | Yuen et al. |
| 7,396,333 B2 | 7/2008 | Stahmann et al. |
| 7,398,115 B2 | 7/2008 | Lynn |
| 7,413,546 B2 | 8/2008 | Agutter et al. |
| 7,425,201 B2 | 9/2008 | Euliano et al. |
| 7,438,072 B2 | 10/2008 | Izuchukwu |
| 7,445,601 B2 | 11/2008 | Kline |
| 7,454,250 B1 | 11/2008 | Bjorling |
| 7,467,012 B1 | 12/2008 | Park et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,479,114 B2 | 1/2009 | Hartley et al. |
| 7,487,774 B2 | 2/2009 | Acker |
| 7,487,778 B2 | 2/2009 | Freitag |
| 7,493,175 B2 | 2/2009 | Cates et al. |
| 7,495,546 B2 | 2/2009 | Lintell et al. |
| 7,499,750 B2 | 3/2009 | Haefner et al. |
| 7,499,758 B2 | 3/2009 | Cates et al. |
| 7,510,531 B2 | 3/2009 | Lee et al. |
| 7,516,742 B2 | 4/2009 | Stenzler et al. |
| 7,520,279 B2 | 4/2009 | Berthon-Jones |
| 7,523,752 B2 | 4/2009 | Montgomery et al. |
| 7,529,592 B2 | 5/2009 | Cates et al. |
| 7,532,934 B2 | 5/2009 | Lee et al. |
| 7,533,670 B1 | 5/2009 | Freitag et al. |
| 7,547,285 B2 | 6/2009 | Kline |
| 7,552,731 B2 | 6/2009 | Jorczak et al. |
| 7,555,335 B2 | 6/2009 | Kamath et al. |
| 7,556,038 B2 | 7/2009 | Kirby et al. |
| 7,562,657 B2 | 7/2009 | Blanch et al. |
| 7,566,318 B2 | 7/2009 | Haefner |
| 7,570,997 B2 | 8/2009 | Lovett et al. |
| 7,572,225 B2 | 8/2009 | Stahmann et al. |
| 7,575,553 B2 | 8/2009 | Stahmann et al. |
| 7,578,293 B2 | 8/2009 | Matthiessen et al. |
| 7,578,794 B2 | 8/2009 | Hatlestad et al. |
| 7,588,033 B2 | 9/2009 | Wondka |
| 7,588,543 B2 | 9/2009 | Euliano et al. |
| 7,591,265 B2 | 9/2009 | Lee et al. |
| 7,591,830 B2 | 9/2009 | Rutter |
| 7,603,631 B2 | 10/2009 | Bermudez et al. |
| 7,610,094 B2 | 10/2009 | Stahmann et al. |
| 7,616,988 B2 | 11/2009 | Stahmann et al. |
| 7,621,270 B2 | 11/2009 | Morris et al. |
| 7,640,932 B2 | 1/2010 | Curti et al. |
| 7,654,966 B2 | 2/2010 | Westinskow et al. |
| 7,662,101 B2 | 2/2010 | Lee et al. |
| 7,662,106 B2 | 2/2010 | Daniels et al. |
| 7,664,546 B2 | 2/2010 | Hartley et al. |
| 7,668,591 B2 | 2/2010 | Lee et al. |
| 7,678,061 B2 | 3/2010 | Lee et al. |
| 7,680,537 B2 | 3/2010 | Stahmann et al. |
| 7,681,573 B2 | 3/2010 | Matthiessen et al. |
| 7,682,312 B2 | 3/2010 | Lurie |
| 7,693,697 B2 | 4/2010 | Westenskow et al. |
| 7,699,788 B2 | 4/2010 | Kuck et al. |
| 7,702,399 B2 | 4/2010 | Heil et al. |
| 7,703,455 B2 | 4/2010 | Bunke et al. |
| 7,704,211 B1 | 4/2010 | Koh |
| 7,713,211 B2 | 5/2010 | Anderson et al. |
| 7,715,916 B2 | 5/2010 | Haefner |
| 7,717,113 B2 | 5/2010 | Andrieux |
| 7,720,541 B2 | 5/2010 | Stahmann et al. |
| 7,721,736 B2 | 5/2010 | Urias et al. |
| 7,722,546 B2 | 5/2010 | Madaus et al. |
| 7,729,757 B2 | 6/2010 | Parascandola et al. |
| 7,735,486 B2 | 6/2010 | Payne |
| 7,735,492 B2 | 6/2010 | Doshi et al. |
| 7,757,690 B2 | 7/2010 | Stahmann et al. |
| 7,758,503 B2 | 7/2010 | Lynn et al. |
| 7,770,580 B2 | 8/2010 | Krüger et al. |
| 7,775,207 B2 | 8/2010 | Jaffe et al. |
| 7,779,834 B2 | 8/2010 | Calluaud et al. |
| 7,784,461 B2 | 8/2010 | Figueiredo et al. |
| 7,787,946 B2 | 8/2010 | Stahmann et al. |
| 7,793,656 B2 | 9/2010 | Johnson |
| 7,793,659 B2 | 9/2010 | Breen |
| 7,798,145 B2 | 9/2010 | Weismann et al. |
| 7,802,571 B2 | 9/2010 | Tehrani |
| 7,810,496 B2 | 10/2010 | Estes et al. |
| 7,810,497 B2 | 10/2010 | Pittman et al. |
| 7,810,498 B1 | 10/2010 | Patterson |
| 7,819,815 B2 | 10/2010 | Younes |
| 7,850,619 B2 | 12/2010 | Gavish et al. |
| 7,861,717 B1 | 1/2011 | Krebs |
| 7,865,233 B2 | 1/2011 | Haefner |
| 7,866,318 B2 | 1/2011 | Bassin |
| 7,885,771 B2 | 2/2011 | Roecker et al. |
| 7,886,740 B2 | 2/2011 | Thomas et al. |
| 7,887,490 B2 | 2/2011 | Danehorn et al. |
| 7,887,493 B2 | 2/2011 | Stahmann et al. |
| 7,938,114 B2 | 5/2011 | Matthews et al. |
| 7,963,283 B2 | 6/2011 | Sinderby |
| 7,970,475 B2 | 6/2011 | Tehrani et al. |
| 7,984,712 B2 | 7/2011 | Soliman et al. |
| 7,992,564 B2 | 8/2011 | Doshi et al. |
| 7,997,271 B2 | 8/2011 | Hickle et al. |
| 8,002,711 B2 | 8/2011 | Wood et al. |
| 8,021,308 B2 | 9/2011 | Carlson et al. |
| 8,021,309 B2 | 9/2011 | Zilberg |
| 8,478,413 B2 | 7/2013 | Splett |
| 8,695,593 B2 | 4/2014 | Tehrani |
| 8,897,879 B2 | 11/2014 | Splett |
| 9,533,113 B2 | 1/2017 | Lain |

(56) References Cited

U.S. PATENT DOCUMENTS

| | | |
|---|---|---|
| 10,194,978 B2 | 2/2019 | Coulombe |
| 10,245,399 B2 | 4/2019 | Martin |
| 10,300,232 B2 | 5/2019 | Bassin |
| 2001/0035186 A1 | 11/2001 | Hill |
| 2002/0017301 A1 | 2/2002 | Lundin |
| 2002/0042564 A1 | 4/2002 | Cooper et al. |
| 2002/0042565 A1 | 4/2002 | Cooper et al. |
| 2002/0069877 A1 | 6/2002 | Villareal et al. |
| 2002/0087057 A1 | 7/2002 | Lovejoy et al. |
| 2002/0153006 A1 | 10/2002 | Zimlich et al. |
| 2002/0153009 A1 | 10/2002 | Chornyj et al. |
| 2002/0185126 A1 | 12/2002 | Krebs |
| 2002/0188332 A1 | 12/2002 | Lurie |
| 2002/0190863 A1 | 12/2002 | Lynn |
| 2003/0000526 A1 | 1/2003 | Gobel |
| 2003/0062040 A1 | 4/2003 | Lurie et al. |
| 2003/0106553 A1 | 6/2003 | Vanderveen |
| 2003/0140925 A1 | 7/2003 | Sapienza et al. |
| 2003/0176804 A1 | 9/2003 | Melker |
| 2003/0190023 A1 | 10/2003 | Farkas et al. |
| 2003/0195571 A1 | 10/2003 | Burnes |
| 2003/0225339 A1 | 12/2003 | Orr et al. |
| 2004/0003814 A1 | 1/2004 | Banner et al. |
| 2004/0045552 A1 | 3/2004 | Curti et al. |
| 2004/0050387 A1 | 3/2004 | Younes |
| 2004/0116784 A1 | 6/2004 | Gavish |
| 2004/0144383 A1 | 7/2004 | Thomas et al. |
| 2004/0149282 A1 | 8/2004 | Hickle |
| 2004/0204734 A1 | 10/2004 | Wagner et al. |
| 2004/0204735 A1 | 10/2004 | Shiroff et al. |
| 2004/0215239 A1 | 10/2004 | Favet et al. |
| 2004/0215240 A1 | 10/2004 | Lovett et al. |
| 2004/0220626 A1 | 11/2004 | Wagner |
| 2004/0220628 A1 | 11/2004 | Wagner |
| 2004/0230229 A1 | 11/2004 | Lovett et al. |
| 2004/0230230 A1 | 11/2004 | Lindstrom et al. |
| 2004/0230249 A1 | 11/2004 | Haefner |
| 2004/0230272 A1 | 11/2004 | Cates et al. |
| 2004/0230282 A1 | 11/2004 | Cates et al. |
| 2004/0236240 A1 | 11/2004 | Kraus et al. |
| 2004/0244804 A1 | 12/2004 | Olsen et al. |
| 2005/0004615 A1 | 1/2005 | Sanders |
| 2005/0039748 A1 | 2/2005 | Andrieux |
| 2005/0042589 A1 | 2/2005 | Hatlestad et al. |
| 2005/0043652 A1 | 2/2005 | Lovett et al. |
| 2005/0061323 A1 | 3/2005 | Lee et al. |
| 2005/0062609 A9 | 3/2005 | Lynn |
| 2005/0065572 A1 | 3/2005 | Hartley et al. |
| 2005/0076908 A1 | 4/2005 | Lee et al. |
| 2005/0080348 A1 | 4/2005 | Stahmann et al. |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0107838 A1 | 5/2005 | Lovett et al. |
| 2005/0109339 A1 | 5/2005 | Stahmann et al. |
| 2005/0121035 A1 | 6/2005 | Martin |
| 2005/0137645 A1 | 6/2005 | Voipio et al. |
| 2005/0139213 A1 | 6/2005 | Blike |
| 2005/0142070 A1 | 6/2005 | Hartley et al. |
| 2005/0215844 A1 | 9/2005 | Ten Eyck et al. |
| 2005/0279358 A1 | 12/2005 | Richey, II |
| 2006/0009708 A1 | 1/2006 | Rapoport et al. |
| 2006/0021618 A1 | 2/2006 | Berthon-Jones et al. |
| 2006/0060198 A1 | 3/2006 | Aylsworth et al. |
| 2006/0122662 A1 | 6/2006 | Tehrani et al. |
| 2006/0129055 A1 | 6/2006 | Orr et al. |
| 2006/0142815 A1 | 6/2006 | Tehrani et al. |
| 2006/0144397 A1 | 7/2006 | Wallace et al. |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0178591 A1 | 8/2006 | Hempfling |
| 2006/0189880 A1 | 8/2006 | Lynn et al. |
| 2006/0195041 A1 | 8/2006 | Lynn et al. |
| 2006/0196507 A1 | 9/2006 | Bradley |
| 2006/0196508 A1 | 9/2006 | Chalvignac |
| 2006/0225737 A1 | 10/2006 | Iobbi |
| 2006/0235324 A1 | 10/2006 | Lynn |
| 2006/0241708 A1 | 10/2006 | Boute |
| 2006/0243275 A1 | 11/2006 | Ruckdeschel et al. |
| 2006/0249148 A1 | 11/2006 | Younes |
| 2006/0249151 A1 | 11/2006 | Gambone |
| 2006/0253038 A1 | 11/2006 | Kuck et al. |
| 2006/0272642 A1 | 12/2006 | Chalvignac |
| 2007/0017510 A1 | 1/2007 | Riedo |
| 2007/0017518 A1 | 1/2007 | Farrugia et al. |
| 2007/0021795 A1 | 1/2007 | Tehrani |
| 2007/0044805 A1 | 3/2007 | Wedler et al. |
| 2007/0062531 A1 | 3/2007 | Fisher et al. |
| 2007/0062532 A1 | 3/2007 | Choncholas |
| 2007/0062533 A1 | 3/2007 | Choncholas et al. |
| 2007/0066961 A1 | 3/2007 | Rutter |
| 2007/0068528 A1 | 3/2007 | Bohm et al. |
| 2007/0078357 A1 | 4/2007 | Kline |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0123792 A1 | 5/2007 | Kline |
| 2007/0129646 A1 | 6/2007 | Heinonen et al. |
| 2007/0129647 A1 | 6/2007 | Lynn |
| 2007/0129666 A1 | 6/2007 | Barton et al. |
| 2007/0149860 A1 | 6/2007 | Lynn et al. |
| 2007/0157931 A1 | 7/2007 | Parker et al. |
| 2007/0167853 A1 | 7/2007 | Melker et al. |
| 2007/0181122 A1 | 8/2007 | Mulier |
| 2007/0191697 A1 | 8/2007 | Lynn et al. |
| 2007/0203448 A1 | 8/2007 | Melker et al. |
| 2007/0221222 A1 | 9/2007 | Lurie |
| 2007/0232951 A1 | 10/2007 | Euliano et al. |
| 2007/0255160 A1 | 11/2007 | Daly |
| 2007/0265611 A1 | 11/2007 | Ignagni |
| 2007/0272242 A1 | 11/2007 | Sanborn et al. |
| 2007/0272243 A1 | 11/2007 | Sherman et al. |
| 2007/0277823 A1 | 12/2007 | Al-Ali et al. |
| 2008/0000475 A1 | 1/2008 | Hill |
| 2008/0011301 A1 | 1/2008 | Qian |
| 2008/0017189 A1 | 1/2008 | Ruckdeschel et al. |
| 2008/0029097 A1 | 2/2008 | Schatzl |
| 2008/0033304 A1 | 2/2008 | Dalal et al. |
| 2008/0033661 A1 | 2/2008 | Syroid et al. |
| 2008/0035145 A1 | 2/2008 | Adams et al. |
| 2008/0039735 A1 | 2/2008 | Hickerson |
| 2008/0041371 A1 | 2/2008 | Freitag |
| 2008/0041383 A1 | 2/2008 | Matthews et al. |
| 2008/0060656 A1 | 3/2008 | Isaza |
| 2008/0071317 A1 | 3/2008 | Stahmann et al. |
| 2008/0077033 A1 | 3/2008 | Figueiredo et al. |
| 2008/0091117 A1 | 4/2008 | Choncholas et al. |
| 2008/0091242 A1 | 4/2008 | Kamath et al. |
| 2008/0110461 A1 | 5/2008 | Mulqueeny et al. |
| 2008/0110462 A1 | 5/2008 | Chekal et al. |
| 2008/0121231 A1 | 5/2008 | Sinderby et al. |
| 2008/0135044 A1 | 6/2008 | Freitag et al. |
| 2008/0139948 A1 | 6/2008 | Stahmann et al. |
| 2008/0161878 A1 | 7/2008 | Tehrani |
| 2008/0163872 A1 | 7/2008 | Negele et al. |
| 2008/0168990 A1 | 7/2008 | Cooke et al. |
| 2008/0183095 A1 | 7/2008 | Austin et al. |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0194980 A1 | 8/2008 | Gisolf et al. |
| 2008/0202525 A1 | 8/2008 | Mitton et al. |
| 2008/0202526 A1 | 8/2008 | Heinonen |
| 2008/0208281 A1 | 8/2008 | Tehrani et al. |
| 2008/0221468 A1 | 9/2008 | Stahmann et al. |
| 2008/0228096 A1 | 9/2008 | Jaffe et al. |
| 2008/0230065 A1 | 9/2008 | Heinonen |
| 2008/0236581 A1 | 10/2008 | Rantala et al. |
| 2008/0236582 A1 | 10/2008 | Tehrani |
| 2008/0275340 A1 | 11/2008 | Beach et al. |
| 2008/0276939 A1 | 11/2008 | Tiedje |
| 2008/0283060 A1 | 11/2008 | Bassin |

(56) References Cited

U.S. PATENT DOCUMENTS

| | | |
|---|---|---|
| 2008/0283061 A1 | 11/2008 | Tiedje |
| 2008/0287756 A1 | 11/2008 | Lynn |
| 2008/0295837 A1 | 12/2008 | McCormick et al. |
| 2008/0295839 A1 | 12/2008 | Habashi |
| 2008/0308105 A1 | 12/2008 | Alder et al. |
| 2008/0312548 A1 | 12/2008 | Hartley et al. |
| 2009/0007914 A1 | 1/2009 | Bateman |
| 2009/0013999 A1 | 1/2009 | Bassin |
| 2009/0014001 A1 | 1/2009 | Myklebust et al. |
| 2009/0020120 A1 | 1/2009 | Schatzl et al. |
| 2009/0020128 A1 | 1/2009 | Metzger et al. |
| 2009/0024008 A1 | 1/2009 | Brunner et al. |
| 2009/0038617 A1 | 2/2009 | Berthon-Jones et al. |
| 2009/0048497 A1 | 2/2009 | Keren |
| 2009/0050148 A1 | 2/2009 | Heinonen et al. |
| 2009/0050151 A1 | 2/2009 | Fuhrman |
| 2009/0050152 A1 | 2/2009 | Iobbi |
| 2009/0054798 A1 | 2/2009 | Varney et al. |
| 2009/0076347 A1 | 3/2009 | Anderson et al. |
| 2009/0078258 A1 | 3/2009 | Bowman et al. |
| 2009/0095297 A1 | 4/2009 | Hallett |
| 2009/0095300 A1 | 4/2009 | McMorrow |
| 2009/0107501 A1 | 4/2009 | Krieger |
| 2009/0107502 A1 | 4/2009 | Younes |
| 2009/0112116 A1 | 4/2009 | Lee et al. |
| 2009/0114223 A1 | 5/2009 | Bonassa |
| 2009/0114224 A1 | 5/2009 | Handzsuj et al. |
| 2009/0118633 A1 | 5/2009 | Jaffe et al. |
| 2009/0120435 A1 | 5/2009 | Slessarev et al. |
| 2009/0133695 A1 | 5/2009 | Rao et al. |
| 2009/0133696 A1 | 5/2009 | Remmers et al. |
| 2009/0137919 A1 | 5/2009 | Bar-Lavie et al. |
| 2009/0139522 A1 | 6/2009 | Thomson et al. |
| 2009/0143694 A1 | 6/2009 | Krauss et al. |
| 2009/0149723 A1 | 6/2009 | Krauss et al. |
| 2009/0151726 A1 | 6/2009 | Freitag |
| 2009/0177702 A1 | 7/2009 | Stahmann et al. |
| 2009/0188502 A1 | 7/2009 | Tiedje |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0199855 A1 | 8/2009 | Davenport |
| 2009/0205660 A1 | 8/2009 | Thomson et al. |
| 2009/0221926 A1 | 9/2009 | Younes |
| 2009/0240098 A1 | 9/2009 | Ten Eyck et al. |
| 2009/0250055 A1 | 10/2009 | Radomski et al. |
| 2009/0250062 A1 | 10/2009 | Reynolds |
| 2009/0255533 A1 | 10/2009 | Freitag et al. |
| 2009/0259135 A1 | 10/2009 | Stasz |
| 2009/0260625 A1 | 10/2009 | Wondka |
| 2009/0266360 A1 | 10/2009 | Acker et al. |
| 2009/0270750 A1 | 10/2009 | Kamath et al. |
| 2009/0272382 A1 | 11/2009 | Euliano et al. |
| 2009/0275808 A1 | 11/2009 | DiMaio et al. |
| 2009/0275841 A1 | 11/2009 | Melendez et al. |
| 2009/0277448 A1 | 11/2009 | Ahlmén et al. |
| 2009/0281433 A1 | 11/2009 | Saadat et al. |
| 2009/0293877 A1 | 12/2009 | Blanch et al. |
| 2009/0299430 A1 | 12/2009 | Davies et al. |
| 2009/0301488 A1 | 12/2009 | Sun |
| 2009/0306527 A1 | 12/2009 | Kubo et al. |
| 2009/0308393 A1 | 12/2009 | Luceros |
| 2009/0308394 A1 | 12/2009 | Levi |
| 2009/0308395 A1 | 12/2009 | Lee et al. |
| 2010/0008466 A1 | 1/2010 | Balakin |
| 2010/0010378 A1 | 1/2010 | Hatlestad et al. |
| 2010/0016750 A1 | 1/2010 | Anderson et al. |
| 2010/0031959 A1 | 2/2010 | Avidor et al. |
| 2010/0186744 A1 | 2/2010 | Bourdon |
| 2010/0076322 A1 | 3/2010 | Shrivastav et al. |
| 2010/0076323 A1 | 3/2010 | Shrivastav et al. |
| 2010/0078019 A1 | 4/2010 | Rittner et al. |
| 2010/0079292 A1 | 4/2010 | Lynn et al. |
| 2010/0083966 A1 | 4/2010 | Jerichow |
| 2010/0083968 A1 | 4/2010 | Wondka et al. |
| 2010/0089396 A1 | 4/2010 | Richard et al. |
| 2010/0099999 A1 | 4/2010 | Hemnes et al. |
| 2010/0106211 A1 | 4/2010 | Lee et al. |
| 2010/0108066 A1 | 5/2010 | Martin et al. |
| 2010/0116270 A1 | 5/2010 | Edwards et al. |
| 2010/0125227 A1 | 5/2010 | Bird |
| 2010/0137732 A1 | 6/2010 | Haveri |
| 2010/0145165 A1 | 6/2010 | Merry |
| 2010/0024820 A1 | 7/2010 | Andrieux |
| 2010/0174154 A1 | 7/2010 | Lee et al. |
| 2010/0174207 A1 | 7/2010 | Lee et al. |
| 2010/0174335 A1 | 7/2010 | Stahmann et al. |
| 2010/0179613 A1 | 7/2010 | Stahmann et al. |
| 2010/0191127 A1 | 7/2010 | Keren et al. |
| 2010/0198289 A1 | 8/2010 | Kameli et al. |
| 2010/0198296 A1* | 8/2010 | Ignagni ............ A61B 5/389 607/42 |
| 2010/0212675 A1 | 8/2010 | Walling et al. |
| 2010/0217140 A1 | 8/2010 | Avidor et al. |
| 2010/0218766 A1 | 9/2010 | Milne |
| 2010/0222650 A1 | 9/2010 | Tanishima et al. |
| 2010/0222693 A1 | 9/2010 | Eriksen et al. |
| 2010/0234705 A1 | 9/2010 | Lynn |
| 2010/0249559 A1 | 9/2010 | Lovejoy et al. |
| 2010/0249584 A1 | 9/2010 | Albertelli |
| 2010/0252043 A1 | 10/2010 | Freitag |
| 2010/0252046 A1 | 10/2010 | Dahlström et al. |
| 2010/0258124 A1 | 10/2010 | Madaus et al. |
| 2010/0262035 A1 | 10/2010 | Subramanian |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282259 A1 | 11/2010 | Figueiredo et al. |
| 2010/0292544 A1 | 11/2010 | Sherman et al. |
| 2010/0300445 A1 | 12/2010 | Chatburn et al. |
| 2010/0305464 A1 | 12/2010 | Ratner |
| 2010/0324437 A1 | 12/2010 | Freeman et al. |
| 2010/0324438 A1 | 12/2010 | Ni et al. |
| 2010/0331715 A1 | 12/2010 | Addison et al. |
| 2011/0004113 A1 | 1/2011 | Jerichow |
| 2011/0009762 A1 | 1/2011 | Eichler et al. |
| 2011/0009763 A1 | 1/2011 | Levitsky et al. |
| 2011/0015501 A1 | 1/2011 | Lynn et al. |
| 2011/0017214 A1 | 1/2011 | Tehrani |
| 2011/0030686 A1 | 2/2011 | Wilkinson et al. |
| 2011/0041847 A1 | 2/2011 | Cosic |
| 2011/0067698 A1 | 3/2011 | Zheng et al. |
| 2011/0073112 A1 | 3/2011 | DiBlasi et al. |
| 2011/0092839 A1 | 4/2011 | Alshaer et al. |
| 2011/0092841 A1 | 4/2011 | Bassin |
| 2011/0100365 A1 | 5/2011 | Wedler et al. |
| 2011/0112424 A1 | 5/2011 | Kesselman et al. |
| 2011/0112425 A1 | 5/2011 | Muhlsteff et al. |
| 2011/0132363 A1 | 6/2011 | Chalvignac |
| 2011/0190845 A1 | 8/2011 | Weisfeldt |
| 2011/0197884 A1 | 8/2011 | Duff et al. |
| 2011/0208082 A1 | 8/2011 | Madaus et al. |
| 2011/0226248 A1 | 9/2011 | Duff et al. |
| 2011/0230780 A1 | 9/2011 | Sanborn et al. |
| 2011/0265793 A1 | 11/2011 | Haveri |
| 2011/0288431 A1 | 11/2011 | Alshaer et al. |
| 2011/0288609 A1 | 11/2011 | Tehrani |
| 2011/0313263 A1 | 12/2011 | Wood et al. |
| 2012/0016252 A1 | 1/2012 | Melker et al. |
| 2012/0029362 A1 | 2/2012 | Patangay et al. |
| 2012/0037159 A1 | 2/2012 | Mulqueeny et al. |
| 2012/0101399 A1 | 4/2012 | Henderson |
| 2012/0123219 A1 | 5/2012 | Georgiev et al. |
| 2012/0136270 A1 | 5/2012 | Leuthardt et al. |
| 2012/0165889 A1 | 6/2012 | Zhang et al. |
| 2013/0030498 A1 | 1/2013 | Tehrani |
| 2013/0116743 A1 | 5/2013 | Karamanoglu |
| 2015/0202448 A1 | 7/2015 | Hoffer |
| 2016/0310730 A1 | 10/2016 | Martins |

(56) References Cited

U.S. PATENT DOCUMENTS

| | | | |
|---|---|---|---|
| 2019/0001127 | A1 | 1/2019 | Evans |
| 2019/0030333 | A1 | 1/2019 | Meyyappan |

FOREIGN PATENT DOCUMENTS

| | | |
|---|---|---|
| CA | 2159564 | 3/1997 |
| CN | 1960671 | 5/2007 |
| CN | 100544670 C | 9/2009 |
| DE | 69121781 | 12/1991 |
| DE | 10213905 | 10/2002 |
| EP | 0459647 | 12/1991 |
| EP | 1715787 | 11/2006 |
| EP | 1972356 | 9/2008 |
| ES | 2094198 | 12/1991 |
| JP | 04231067 | 8/1992 |
| JP | 3183527 | 7/2001 |
| WO | WO 9404071 | 3/1994 |
| WO | WO 9831282 | 7/1998 |
| WO | WO 200020379 | 4/2000 |
| WO | WO 200021597 | 4/2000 |
| WO | WO 200142895 | 6/2001 |
| WO | WO 200162148 | 8/2001 |
| WO | WO 200231642 | 4/2002 |
| WO | WO 200232036 | 4/2002 |
| WO | WO 02/45566 | 6/2002 |
| WO | WO 03026501 | 4/2003 |
| WO | WO 03030724 | 4/2003 |
| WO | WO 2004019766 | 3/2004 |
| WO | WO 2004032727 | 4/2004 |
| WO | WO 2004060166 | 7/2004 |
| WO | WO 2004069317 | 8/2004 |
| WO | WO 2004091715 | 10/2004 |
| WO | WO 2004091717 | 10/2004 |
| WO | WO 2004091719 | 10/2004 |
| WO | WO 2004091720 | 10/2004 |
| WO | WO 2005014091 | 2/2005 |
| WO | WO 2005018737 | 3/2005 |
| WO | WO 2005028029 | 3/2005 |
| WO | WO 2005051280 | 6/2005 |
| WO | WO 200577268 | 8/2005 |
| WO | WO 2005089638 | 9/2005 |
| WO | WO 2005102450 | 11/2005 |
| WO | WO 2006012205 | 2/2006 |
| WO | WO 2006018237 | 2/2006 |
| WO | WO 2006047212 | 5/2006 |
| WO | WO 2006054114 | 5/2006 |
| WO | WO 2006110812 | 10/2006 |
| WO | WO 2007012170 | 2/2007 |
| WO | WO 2007012197 | 2/2007 |
| WO | WO 2007026367 | 3/2007 |
| WO | WO 2007035804 | 3/2007 |
| WO | WO 2007058938 | 5/2007 |
| WO | WO 2007085109 | 8/2007 |
| WO | WO 2007088885 | 8/2007 |
| WO | WO 2007096181 | 8/2007 |
| WO | WO 2007109443 | 9/2007 |
| WO | WO 2007122406 | 11/2007 |
| WO | WO 2008012509 | 1/2008 |
| WO | WO 2008019102 | 2/2008 |
| WO | WO 2008039691 | 4/2008 |
| WO | WO 2008082314 | 7/2008 |
| WO | WO 2008083842 | 7/2008 |
| WO | WO 2008102362 | 8/2008 |
| WO | WO 2008106961 | 9/2008 |
| WO | WO 2008107899 | 9/2008 |
| WO | WO 2008112927 | 9/2008 |
| WO | WO 2008129535 | 10/2008 |
| WO | WO 2009022330 | 2/2009 |
| WO | WO 2009026562 | 2/2009 |
| WO | WO 2009036312 | 3/2009 |
| WO | WO 2009052631 | 4/2009 |
| WO | WO 2009056457 | 5/2009 |
| WO | WO 2009070186 | 6/2009 |
| WO | WO 2009099939 | 8/2009 |
| WO | WO 2009135081 | 11/2009 |
| WO | WO 2009137520 | 11/2009 |
| WO | WO 2010042253 | 4/2010 |
| WO | WO 2010045295 | 4/2010 |
| WO | WO 10108552 | 9/2010 |
| WO | WO 2010099375 | 9/2010 |
| WO | WO 2010111073 | 9/2010 |
| WO | WO 2018212840 | 11/2018 |

OTHER PUBLICATIONS

Le Pimpec-Barthes, Francoise, et al., "Intrathoracic phrenic packing: A 10-year experience in France", The Journal of Thoracic and Cardiovascular Surgery, Aug. 2011, pp. 378-383.
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Puritan Bennett 980 Series Ventilator Operator's Manual, Covidien, Jan. 29, 2014, Part. No. 10077893 A Jan. 2014, 506 pages.
PCT International Search Report and Written Opinion in International Application PCT/US2020/036048, dated Oct. 5, 2020, 14 pages.

* cited by examiner

ACHIEVING SMOOTH BREATHING BY MODIFIED BILATERAL PHRENIC NERVE PACING

CROSS-REFERENCE TO RELATED APPLICATIONS

This application claims the benefit of U.S. Provisional Application No. 62/868,280, filed Jun. 28, 2019, of which the complete disclosure is hereby incorporated herein by reference in the entirety.

INTRODUCTION

Long term external ventilation is typically provided to patients using positive pressure ventilation. Positive pressure ventilation is a form of artificial respiration in which a mechanical ventilator is used to deliver a controlled volume of gasses to the lungs of a patient. In contrast, in one form of negative-pressure ventilation, the diaphragm of a patient is caused to contract to cause the chest of the patient to expand during inspiration (thereby drawing air into the lungs), and the diaphragm is caused to relax to cause the chest to contract during exhalation (thereby forcing air out of the lungs). While lifesaving and valuable, positive pressure ventilation is non-physiological; that is, forcing air into the lungs is not the manner in which humans naturally breathe. Accordingly, the greater the positive pressure and/or the number of positive-pressure cycles, the more likely the patient will experience detrimental effects, such as an illness becoming more severe, acute respiratory distress syndrome (ARDS), ventilator-associated pneumonia (VAP), diaphragm dystrophy, and delay of ventilator weaning. These detrimental effects may increase an amount of time a patient is subjected to mechanical ventilation, leading to longer hospital stays and increased medical costs.

Achieving Smooth Breathing by Modified Bilateral Phrenic Nerve Pacing

Negative-pressure ventilation leverages the normal physiologic way humans breathe and can be provided by stimulating the phrenic nerves of the diaphragm. However, current protocols for phrenic nerve stimulation have been unsuccessful in achieving smooth breathing patterns but rather cause hiccup-like breathing patterns. While the left diaphragm and the right diaphragm respond differently to pulse stimulation techniques, the two sides are mechanically connected. Accordingly, at least one problem with phrenic nerve stimulation involves stimulating the left and/or right diaphragm in a manner such that smooth breathing patterns may be achieved. That is, flow and volume waveforms for existing phrenic nerve stimulation techniques may be irregular and inconsistent which may cause hiccup-like breathing; therefore, it is desirable to achieve smooth flow and volume breathing patterns when stimulating the phrenic nerves.

In accordance with examples of the present disclosure, a system for stimulating phrenic nerves of a patient to provide smooth breathing is provided. More specifically, by identifying contraction thresholds for each of the left and right portions of a diaphragm, as well as optimal pacing voltages for each of the left and right portions of the diaphragm for a desired tidal volume, a customized pacing signal may be delivered to each of the right and left portions of the diaphragm, where each pacing signal takes into account the contraction thresholds. More specifically, a voltage of a first pacing signal may be below a contraction threshold for a first side of the diaphragm, while a voltage of a second pacing signal may be equal to or greater than a contraction threshold for a second side of the diaphragm. Accordingly, the mechanical interaction of the right and left sides of the diaphragm may be utilized to achieve smooth breathing. Phrenic nerve stimulation may provide a smooth breathing pattern with a desired tidal volume to a patient in the absence of any other breathing support.

In one aspect, the present disclosure provides a method for providing bilateral phrenic nerve pacing. The method may include determining a first contraction threshold at which a first portion of diaphragm muscles contract to draw a first desired tidal volume into lungs of a patient and determining a second contraction threshold at which a second portion of the diaphragm muscles contract to draw a second desired tidal volume into the lungs of the patient. The method may further include generating a first pacing signal having a first amplitude less than the first contraction threshold and delivering the first pacing signal thereby stiffening the first portion of the diaphragm muscles. Additionally, the method may include generating a second pacing signal having a second amplitude equal to or greater than the second contraction threshold and delivering the second pacing signal thereby contracting the second portion of the diaphragm muscles.

In an example, the method may further include delivering a third desired tidal volume to the lungs of the patient. In another example, the first contraction threshold is equal to the second contraction threshold. In a further example, the method includes delivering the first amplitude to the first phrenic nerve with the first pacing signal; and delivering the second amplitude to the second phrenic nerve with the second pacing signal. In yet another example, the method further includes modifying a first output signal having the first contraction threshold until a measured tidal volume is within a first desired range; and modifying a second output signal having the second contraction threshold until a measured tidal volume is within a second desired range. In still another example, the method includes modifying a parameter of the first pacing signal, wherein the parameter is one of: a frequency, a pulse duration, or a pulse shape. In a further example, the first amplitude of the first pacing signal is at least a stiffening voltage greater than zero. In another example, the method includes providing positive pressure ventilation to the patient while generating the first pacing signal and the second pacing signal.

In another aspect, the present disclosure provides a ventilator system. The ventilator system may include a phrenic nerve stimulator performing a set of operations. The set of operations may include determining a first contraction threshold at which a first portion of diaphragm muscles contract to draw a first desired tidal volume into lungs of a patient, and determining a second contraction threshold at which a second portion of the diaphragm muscles contract to draw a second desired tidal volume into the lungs of the patient. The set of operations may further include generating, via at least one signal generator, a first pacing signal having a first amplitude less than the first contraction threshold; and delivering the first pacing signal thereby stiffening the first portion of the diaphragm muscles. Additionally, the set of operations may include generating, via the at least one signal generator; a second pacing signal having a second amplitude equal to or greater than the second contraction threshold; and delivering the second pacing signal thereby contracting the second portion of the diaphragm muscles.

In an example, the set of operations may further include delivering a third desired tidal volume to the lungs of the patient. In another example, the set of operations further includes modifying at least one of the first pacing signal or the second pacing signal, based on a third desired tidal volume. In a further example, modifying the at least one of the first pacing signal or the second pacing signal includes changing at least one of: a frequency, a pulse duration, a pulse shape, or an amplitude. In yet another example, the set of operations further includes delivering the third desired tidal volume. In still a further example, the set of operations further includes modifying a first output signal based on the first threshold until a measured tidal volume is within a range of a third desired tidal volume; and modifying a second output signal based on the second threshold until a measured tidal volume is within a range of the third desired tidal volume. In another example, the ventilator system includes a ventilator chassis configured to provide positive pressure ventilation to the patient. In a further example, the set of operations further includes measuring an end-tidal carbon dioxide measurement associated with a breathing cycle; and modifying at least one of the first pacing signal or the second pacing signal, based on the end-tidal carbon dioxide measurement.

In another aspect, the present disclosure provides a method for generating phrenic nerve pacing signals. The method may include determining a first output signal of a first electrode in proximity to a first phrenic nerve of a patient, and determining a second output signal of a second electrode in proximity to a second phrenic nerve of the patient. The method may further include providing the first output signal, thereby causing a first portion of the patient's diaphragm muscles to stiffen without contracting; and providing the second output signal, thereby causing a second portion of the patient's diaphragm muscles to contract.

In an example, determining the first output signal includes identifying a first contraction threshold at which the first portion of the patient's diaphragm muscles contract to draw a first desired tidal volume into lungs of the patient. In another example, determining the second output signal comprises identifying a second contraction threshold at which the second portion of the patient's diaphragm muscles contract to draw a second desired tidal volume into the lungs of the patient. In a further example, determining the first output signal and determining the second output signal includes: measuring a parameter, while varying an amplitude of the first output signal over a first range and varying an amplitude of the second output signal over a second range; and based on the parameter, identifying a first amplitude of the first output signal and a second amplitude of the second output signal. In yet another example, the first contraction threshold is greater than the second contraction threshold. In still a further example, the method further includes performing an end-tidal carbon dioxide measurement; and modifying the first output signal or the second output signal based on the end-tidal carbon dioxide measurement.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
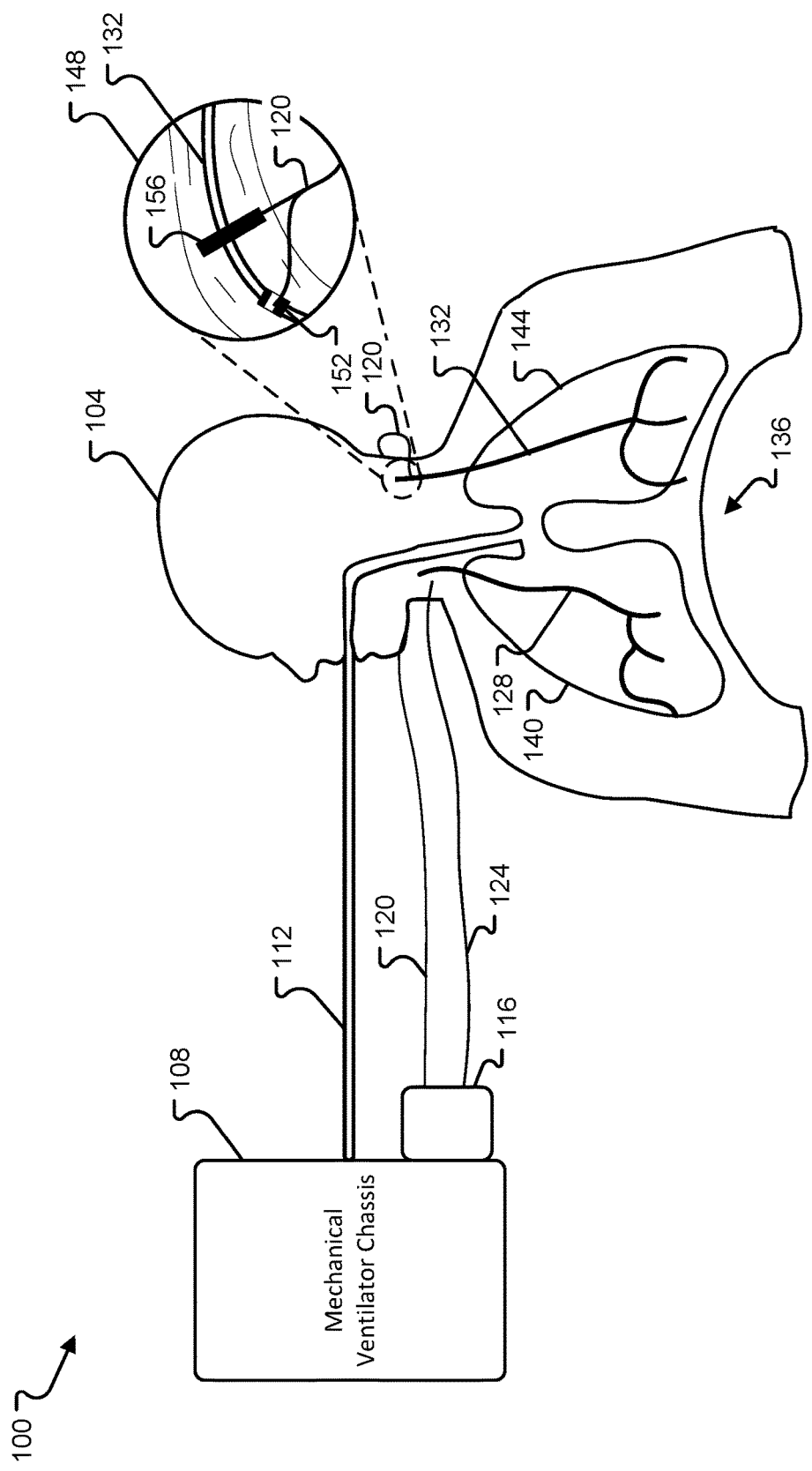
FIG. 1 illustrates a block diagram of a phrenic nerve stimulation system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a block diagram depicting a phrenic nerve stimulation system 100 that achieves smooth breathing with a desired tidal volume. Tidal volume generally refers to an amount of gas passing into or out of the lungs in each respiratory cycle under normal breathing efforts. The phrenic nerve stimulation system 100 may include a ventilator chassis 108 connected or otherwise coupled to a patient 104 via a breathing tube 112. The ventilator chassis 108 may perform functions of a spirometer or otherwise include the ability to measure tidal volume. Alternatively, or in addition, a measurement of a tidal volume is not limited to being provided by the ventilator chassis 108; that is, a tidal volume measurement may be provided by any device, whether part of the ventilator chassis 108 or otherwise, that can measure tidal volume and then make such measurement available. In some examples, the ventilator chassis 108 may be a positive pressure ventilator configured to provide one or more modes of ventilation. As a non-limiting example, the ventilator chassis 108 may provide adaptive support ventilation, pressure support ventilation, and/or proportional assist ventilation, where adaptive support ventilation is a type of positive pressure ventilation that is controlled to automatically adjust based on the patient requirements, pressure support ventilation is a type of positive pressure ventilation in which the patient breathes spontaneously and breathing is augmented with air at a preset amount of pressure, and proportional assist ventilation is a type of positive pressure ventilation in which the ventilator can sense the patient's level of inspiratory flow (or patient effort) and deliver pressure support to achieve a given tidal volume. Other types and modes of ventilation may be provided by the ventilator chassis 108. The phrenic nerve stimulation system 100 further includes a pacing module 116; the pacing module 116 may be integrated into the ventilator chassis 108 and/or provided as an add-on module. The pacing module 116 may be coupled to stimulation leads 120 and 124; electrodes may be coupled to distal portions of each of the stimulation leads 120 and 124 such that the electrodes may be placed in proximity to the right phrenic nerve 128 and/or left phrenic nerve 132.

As illustrated in FIG. 1, there are two phrenic nerves, a right phrenic nerve 128 and a left phrenic nerve 132. The right phrenic nerve 128 and the left phrenic nerve 132 originate from the spinal cord in the neck region (C3-C5 cervical vertebral region) and pass down between the lung and heart to reach the diaphragm 136, where each of the right phrenic nerve 128 and/or the left phrenic nerve 132 pass motor information to the diaphragm 136. As further illustrated in the enlarged portion 148, an electrode 152 may be coupled to a stimulation lead 120, where the electrode 152 is placed adjacent to or otherwise in proximity to the left phrenic nerve 132. The electrode 152 may include one or more dipoles for providing an electrical stimulation to the left phrenic nerve 132. Alternatively, or in addition, an electrode 156 may be placed transverse to the left phrenic nerve 132, where the electrode 156 may include a plurality of dipoles for providing an electrical stimulation to the left phrenic nerve 132. A similar or same configuration may exist for the right phrenic nerve 128; that is one or more electrodes may be coupled to the stimulation lead 124 and may be placed in proximity to the right phrenic nerve 128.

In accordance with examples of the present disclosure, the pacing module 116 may be configured to provide bilateral phrenic nerve pacing. That is, the pacing module 116 may cause one of the right or left side of the diaphragm to stiffen by delivering a pacing signal having a pacing voltage that is just below a first contraction threshold specific to the tight or left side of the diaphragm, respectively; and the pacing module 116 may cause the other one of the right or left side of the diaphragm to contract by delivering a pacing signal having a pacing voltage at or above a second contraction threshold specific for the other one of the right or left side of the diaphragm, respectively. By stiffen, it is meant exciting the phrenic nerve with a signal having a pacing voltage that is below the contraction threshold for the respective diaphragm muscle. Stiffening may be done for the left or right side of the diaphragm muscles by stimulating the corresponding phrenic nerve; however, it is preferred to stiffen the diaphragm muscle having a higher contraction threshold, wherein a contraction threshold may be the lowest voltage that causes a side of the diaphragm to contract for which a minimum acceptable tidal volume is achieved. In some instances, a contraction threshold for one of the sides of the diaphragm 136 may be below the voltage that causes the other side of the diaphragm 136 to contract, while a contraction threshold for the other of the sides of the diaphragm 136 may be equal to or greater than the voltage that causes the other of the left or right side of the diaphragm 136 to contract.

To determine whether the right or left side of the diaphragm has a higher contraction threshold, the pacing module 116 may vary an amplitude of an output signal provided to each of the right phrenic nerve 128 or the left phrenic nerve 132 for different respiratory cycles. For example, an output signal with zero amplitude may be applied to the left phrenic nerve 132 while an output signal with a variable amplitude may be applied to the right phrenic nerve 128 over a plurality of respiratory cycles. As an amplitude of the output signal applied to the right phrenic nerve 128 is varied (for example, increased from zero volts to 0.9 volts), a right side of the diaphragm may stiffen during one respiratory cycle; as the amplitude increases, the right side of the diaphragm may then contract during another respiratory cycle. Accordingly, an amplitude which causes the right side of the diaphragm to contract may be considered to be a first contraction threshold for the right side of the diaphragm. Similarly, an output signal with zero amplitude may be applied to the right phrenic nerve 128 while an output signal with a variable amplitude may be applied to the left phrenic nerve 132 over a plurality of respiratory cycles. As an amplitude of the output signal applied to the left phrenic nerve 128 is varied (for example, increased from zero volts to 0.9 volts), a left side of the diaphragm may stiffen during a respiratory cycle; as the amplitude increases, the left side of the diaphragm may then contract during another respiratory cycle. Accordingly, an amplitude which causes the left side of the diaphragm to contract may be considered to be a second contraction threshold for the left side of the diaphragm. A first pacing signal having a voltage less than the contraction threshold may be applied to the side of the diaphragm having the highest contraction threshold, while a second pacing signal having a voltage that is equal to or greater than the contraction threshold may be applied to the side of the diaphragm having the lowest contraction threshold. In some examples, a first pacing signal having a voltage equal to or greater than the contraction threshold may be applied to the side of the diaphragm having the highest contraction threshold, while a second pacing signal having a voltage less than the contraction threshold may be applied to the side of the diaphragm having the lowest contraction threshold.

In accordance with some examples of the present disclosure, the voltages of the first and second pacing signals may be determined based on tidal volumes and other desired breath characteristics, such as but not limited to end-tidal carbon dioxide (EtCO2), patient work of breath, smooth breath classifications, partial atrial carbon dioxide—whether directly or indirectly indicating a rise in the carbon dioxide level, muscle characteristics, and/or any other physiological characteristic that may relate to or be indicative how a muscle stiffens and/or reacts to a pacing signal. For example, inhalation (Vti) and exhalation (Vte) tidal volumes may be measured as voltages of the first and second pacing signals vary over a plural of respiratory cycles. That is, an amplitude, or voltage, of the pacing signal for the side of the diaphragm having the highest contraction threshold may systematically decrease by a specific amount as an amplitude of the pacing signal for the side of the diaphragm having the lowest contraction threshold systematically increases by a specified amount over a plurality of breathing cycles. Table 1 depicts example inhalation tidal data from porcine experiments as pacing voltages for the left and right phrenic nerves are incrementally varied, where the right phrenic nerve may have a contraction threshold that is above 0.5 volts and the left phrenic nerve may have a contraction threshold that is below 0.4 volts. Table 2 depicts example EtCO2 measurements from the same porcine experiments. Based on Table 1 and Table 2, stimulating the right phrenic nerve with a pacing voltage near 0.4 volts and stimulating the left phrenic nerve with a pacing voltage between 0.4 volts and 0.7 volts may provide good inspiratory volume and EtCO2 measurements. In some examples, the pacing voltages for the left and right phrenic nerves may be based on a ventilation protocol that includes tidal volume, inhalation and exhalation times, and EtCO2 for example.

TABLE 1

| | Vti measurements | | | | |
| --- | --- | --- | --- | --- | --- |
| Left Phrenic Nerve | Right Phrenic Nerve Pacing Voltage (V) | | | | |
| Pacing Voltage (V) | 0.1 | 0.2 | 0.3 | 0.4 | 0.5 |
| 0.4 | 560 ml | 529 ml | 559 ml | 862 ml | 1029 ml |
| 0.5 | 579 ml | 542 ml | 565 ml | 907 ml | 994 ml |
| 0.6 | 617 ml | 594 ml | 565 ml | 979 ml | |
| 0.7 | 627 ml | 599 ml | 576 ml | 987 ml | |
| 0.8 | 631 ml | 613 ml | 596 ml | | |
| 1 | 627 ml | 624 ml | 636 ml | | |

TABLE 2

EtCO2 measurements

| Left Phrenic Nerve Pacing Voltage (V) | Right Phrenic Nerve Pacing Voltage (V) | | | | |
|---|---|---|---|---|---|
| | 0.1 | 0.2 | 0.3 | 0.4 | 0.5 |
| 0.4 | 41 mm HG | 41 mm HG | 40 mm HG | 34 mm HG | 27 mm HG |
| 0.5 | 41 mm HG | 41 mm HG | 41 mm HG | 32 mm HG | 27 mm HG |
| 0.6 | 41 mm HG | 41 mm HG | 42 mm HG | 30 mm HG | 27 mm HG |
| 0.7 | 40 mm HG | 41 mm HG | 40 mm HG | 28 mm HG | |
| 0.8 | 39 mm HG | 40 mm HG | 40 mm HG | | |
| 1 | 39 mm HG | 41 mm HG | 39 mm HG | | |

As depicted in Tables 1 and 2, a voltage of a right phrenic nerve may stay relatively constant while a voltage of the left phrenic nerve increases over a plurality of breathing cycles; accordingly, an inhalation volume may be measured for each breathing cycle. Similarly; a voltage of the right phrenic nerve may vary while a voltage of the left phrenic nerve stays relatively constant over a plurality of breathing cycles; inhalation volumes may be measured for each breathing cycle. In addition to volume related measurements, EtCO2 measurements may be obtained, such as those depicted in Table 2.

As provided in Table 3, data from various voltage levels may be captured and utilized for determining optimal voltages of the first and second pacing signals. As previously discussed, the pacing voltage $V_{P1}$ and $V_{P2}$ may be determined based on desired tidal volumes Vti and Vte, and/or other desired breath characteristics, such as but not limited to end-tidal carbon dioxide (EtCO2), patient work of breath, smooth breath classifications, partial atrial carbon dioxide—whether directly or indirectly indicating a rise in the carbon dioxide level, muscle characteristics, and/or any other physiological characteristic that may relate to or be indicative how a muscle stiffens and/or reacts to a pacing.

TABLE 3

| Pulse amp Right | Pulse amp Left | Pulse width | Pulse freq | PEEP | WOB (pt) J/L | Insp Rise time (s) | I:E | Vti (ml) | Vte (ml) | EtCo2 (mmHg) | Remarks |
|---|---|---|---|---|---|---|---|---|---|---|---|
| 0 | 0.2 V | 100 us | 40 Hz | NA | | | | | | | Apnea |
| 0.5 V | 0 | 100 us | 40 Hz | 5.8 | 0.2 | 0.5 | 1 × 10 | 94 | 91 | 7 | Not felt |
| 0.5 V | 0.2 V | 100 us | 40 Hz | NA | | | | | | | Apnea |
| 0 | 0.25 V | 100 us | 40 Hz | 5.8 | 0.3 | 0.5 | 1 × 7.9 | 227 | 242 | 40 | Very smooth breathing |
| 0.6 V | 0 | 100 us | 40 Hz | 6.3 | 0.4 | 0.5 | 1 × 6.6 | 455 | 487 | 49 | Smooth breathing |
| 0.6 V | 0.25 V | 100 us | 40 Hz | 5.8 | 0.6 | 0.5 | 1 × 7.3 | 550 | 594 | 43 | Smooth breathing |
| 0 | 0.3 V | 100 us | 40 Hz | 6.3 | 0.5 | 0.5 | 1 × 7.4 | 480 | 509 | 43 | Smooth breathing |
| 0.7 V | 0 | 100 us | 40 Hz | 5.8 | 0.6 | 0.5 | 1 × 7.5 | 551 | 584 | 48 | Not smooth |
| 0.7 V | 0.3 V | 100 us | 40 Hz | 5.8 | 0.6 | 0.5 | 1 × 7.6 | 577 | 607 | 44 | Smooth breathing but right side not getting enough volume |
| 0 | 0.4 V | 100 us | 40 Hz | 5.8 | 0.7 | 0.5 | 1 × 7.9 | 544 | 588 | 43 | Not so smooth |
| 0.8 V | 0 | 100 us | 40 Hz | 6.4 | 0.7 | 0.5 | 1 × 6.8 | 612 | 670 | 43 | Not so smooth |
| 0.8 V | 0.4 V | 100 us | 40 Hz | 5.8 | 0.7 | 0.5 | 1 × 8.0 | 580 | 621 | 45 | Smooth breathing |
| 0 | 0.5 V | 100 us | 40 Hz | 5.8 | 0.7 | 0.5 | 1 × 7.8 | 554 | 580 | 43 | Not smooth |
| 0.9 V | 0 | 100 us | 40 Hz | 5.8 | 0.75 | 0.5 | 1 × 7.2 | 600 | 610 | 43 | Not smooth |
| 0.9 V | 0.5 V | 100 us | 40 Hz | 5.8 | 0.7 | 0.5 | 1 × 6.7 | 670 | 733 | 43 | Not smooth |
| 0 | 0.6 V | 100 us | 40 Hz | 6.3 | 0.6 | 0.5 | 1 × 8.2 | 560 | 606 | 47 | Not smooth |
| 1 V | 0 | 100 us | 40 Hz | 5.8 | 0.7 | 0.5 | 1 × 6.2 | 628 | 650 | 41 | Not smooth |
| 1 V | 0.6 V | 100 us | 40 Hz | 5.8 | 0.85 | 0.5 | 1 × 7.9 | 600 | 648 | 43 | Not smooth |
| 0 | 0.7 V | 100 us | 40 Hz | 5.8 | 0.8 | 0.5 | 1 × 8.2 | 593 | 620 | 45 | Strong contraction |
| 2 V | 0 | 100 us | 40 Hz | 5.8 | 1 | 0.5 | 1 × 8.2 | 680 | 684 | 43 | Strong contraction |
| 2 V | 0.7 V | 100 us | 40 Hz | 5.8 | 1.5 | 0.5 | 1 × 3.8 | 1053 | 1120 | 37 | Strong contraction |
| 0 | 1 V | 100 us | 40 Hz | 5.8 | 1.2 | 0.5 | 1 × 6.1 | 1085 | 1147 | 35 | Strong contraction |
| 3 V | 0 | 100 us | 40 Hz | 5.8 | 1 | 0.5 | 1 × 7.7 | 690 | 677 | 41 | Strong contraction |
| 3 V | 1 V | 100 us | 40 Hz | 4.8 | 1.1 | 0.5 | 1 × 6.3 | 1063 | 1176 | 35 | Strong contraction |

With high tidal volumes no further progression was made

As provided in Table 4, additional data from various different voltage levels and for a different pulse width may be captured and utilized for determining optimal voltages of the first and second pacing signals. As previously discussed, the pacing voltage $V_{P1}$ and $V_{P2}$ may be determined based on desired tidal volumes Vti and Vte, and/or other desired breath characteristics, such as but not limited to end-tidal carbon dioxide (EtCO2), patient work of breath, and smooth breath classifications, partial atrial carbon dioxide—whether directly or indirectly indicating a rise in the carbon dioxide level, muscle characteristics, and/or any other physiological characteristic that may relate to or be indicative how a muscle stiffens and/or reacts to a pacing.

TABLE 4

| Pulse amp Right | Pulse amp Left | Pulse width | Pulse freq | PEEP | WOB (pt) J/L | Insp Rise time (s) | I:E | Vti (ml) | Vte (ml) | EtCo2 (mmHg) | Remarks |
| --- | --- | --- | --- | --- | --- | --- | --- | --- | --- | --- | --- |
| 0.1 V | 0.4 V | 1 ms | 40 Hz | 5.9 | 0.5 | 0.5 | 1 × 6.1 | 560 | 610 | 41 | Smooth breathing |
| 0.1 V | 0.5 V | 1 ms | 40 Hz | 6 | 0.6 | 0.5 | 1 × 6.8 | 579 | 632 | 41 | Smooth breathing |
| 0.1 V | 0.6 V | 1 ms | 40 Hz | 5.8 | 0.7 | 0.5 | 1 × 6.8 | 617 | 632 | 41 | Smooth breathing |
| 0.1 V | 0.7 V | 1 ms | 40 Hz | 5.7 | 0.7 | 0.5 | 1 × 7.1 | 627 | 650 | 40 | Smooth breathing |
| 0.1 V | 0.8 V | 1 ms | 40 Hz | 5.8 | 0.7 | 0.5 | 1 × 7.1 | 631 | 668 | 39 | Smooth breathing |
| 0.1 V | 1 V | 1 ms | 40 Hz | 5.8 | 0.7 | 0.5 | 1 × 6.5 | 627 | 656 | 39 | Smooth breathing |
| 0.2 V | 0.4 V | 1 ms | 40 Hz | 5.8 | 0.4 | 0.55 | 1 × 6.3 | 529 | 542 | 41 | Smooth breathing |
| 0.2 V | 0.5 V | 1 ms | 40 Hz | 6 | 0.6 | 0.5 | 1 × 6.7 | 542 | 585 | 41 | Smooth breathing |
| 0.2 V | 0.6 V | 1 ms | 40 Hz | 5.8 | 0.6 | 0.5 | 1 × 6.8 | 594 | 613 | 41 | Smooth breathing |
| 0.2 V | 0.7 V | 1 ms | 40 Hz | 6 | 0.6 | 0.5 | 1 × 7.0 | 599 | 610 | 41 | Smooth breathing |
| 0.2 V | 0.8 V | 1 ms | 40 Hz | 5.7 | 0.6 | 0.5 | 1 × 7.2 | 613 | 628 | 40 | Smooth breathing |
| 0.2 V | 1 V | 1 ms | 40 Hz | 6 | 0.7 | 0.5 | 1 × 6.8 | 624 | 643 | 41 | Smooth breathing |
| 0.3 V | 0.4 V | 1 ms | 40 Hz | 5.8 | 0.5 | 0.55 | 1 × 5.7 | 559 | 579 | 40 | Smooth breathing |
| 0.3 V | 0.5 V | 1 ms | 40 Hz | 5.8 | 0.4 | 0.58 | 1 × 6.4 | 565 | 579 | 41 | Smooth breathing |
| 0.3 V | 0.6 V | 1 ms | 40 Hz | 5.8 | 0.6 | 0.5 | 1 × 6.6 | 565 | 596 | 42 | Smooth breathing |
| 0.3 V | 0.7 V | 1 ms | 40 Hz | 5.8 | 0.6 | 0.5 | 1 × 7.0 | 576 | 611 | 40 | Smooth breathing |
| 0.3 V | 0.8 V | 1 ms | 40 Hz | 6 | 0.6 | 0.5 | 1 × 6.9 | 596 | 626 | 40 | Smooth breathing |
| 0.3 V | 1 V | 1 ms | 40 Hz | 5.7 | 0.7 | 0.5 | 1 × 6.7 | 636 | 655 | 39 | Smooth breathing |
| 0.4 V | 0.4 V | 1 ms | 40 Hz | 5.8 | 0.7 | 0.65 | 1 × 4.8 | 862 | 920 | 34 | Smooth breathing |
| 0.4 V | 0.5 V | 1 ms | 40 Hz | 5.7 | 0.8 | 0.7 | 1 × 5 | 907 | 959 | 32 | Smooth breathing |
| 0.4 V | 0.6 V | 1 ms | 40 Hz | 5.1 | 0.8 | 0.64 | 1 × 5.2 | 979 | 1024 | 30 | Smooth but strong breathing |
| 0.4 V | 0.7 V | 1 ms | 40 Hz | 5.7 | 1 | 0.63 | 1 × 5.3 | 987 | 1064 | 28 | Smooth but strong breathing |
| 0.4 V | 0.8 V | 1 ms | 40 Hz | Cancelled due to very high tidal volumes | | | | | | | |
| 0.4 V | 1 V | 1 ms | 40 Hz | | | | | | | | |
| 0.5 V | 0.4 V | 1 ms | 40 Hz | 5.7 | 0.5 | 0.55 | 1 × 5.7 | 1029 | 1060 | 27 | Smooth but strong breathing |
| 0.5 V | 0.5 V | 1 ms | 40 Hz | 5.7 | 0.4 | 0.58 | 1 × 6.4 | 994 | 1069 | 27 | Smooth but strong breathing |
| 0.5 V | 0.6 V | 1 ms | 40 Hz | 5.7 | 0.6 | 0.5 | 1 × 6.6 | | 1055 | 27 | Smooth but strong breathing |

No further pacing done as tidal volume was very high

Figure 2A:
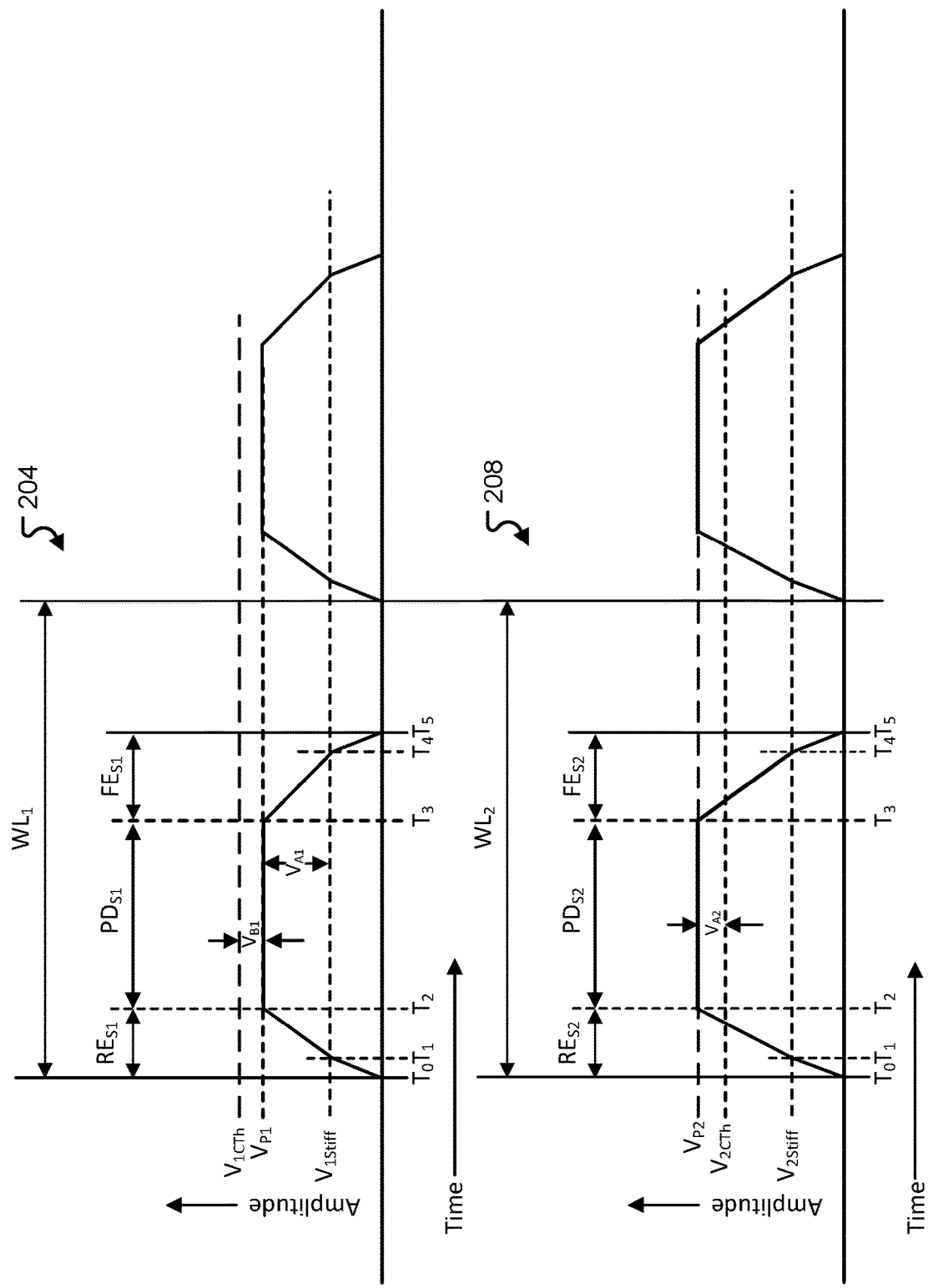
FIGS. 2A-2B depict example pacing signals having pacing voltages generated by the phrenic nerve stimulation system.
Figure 2B:
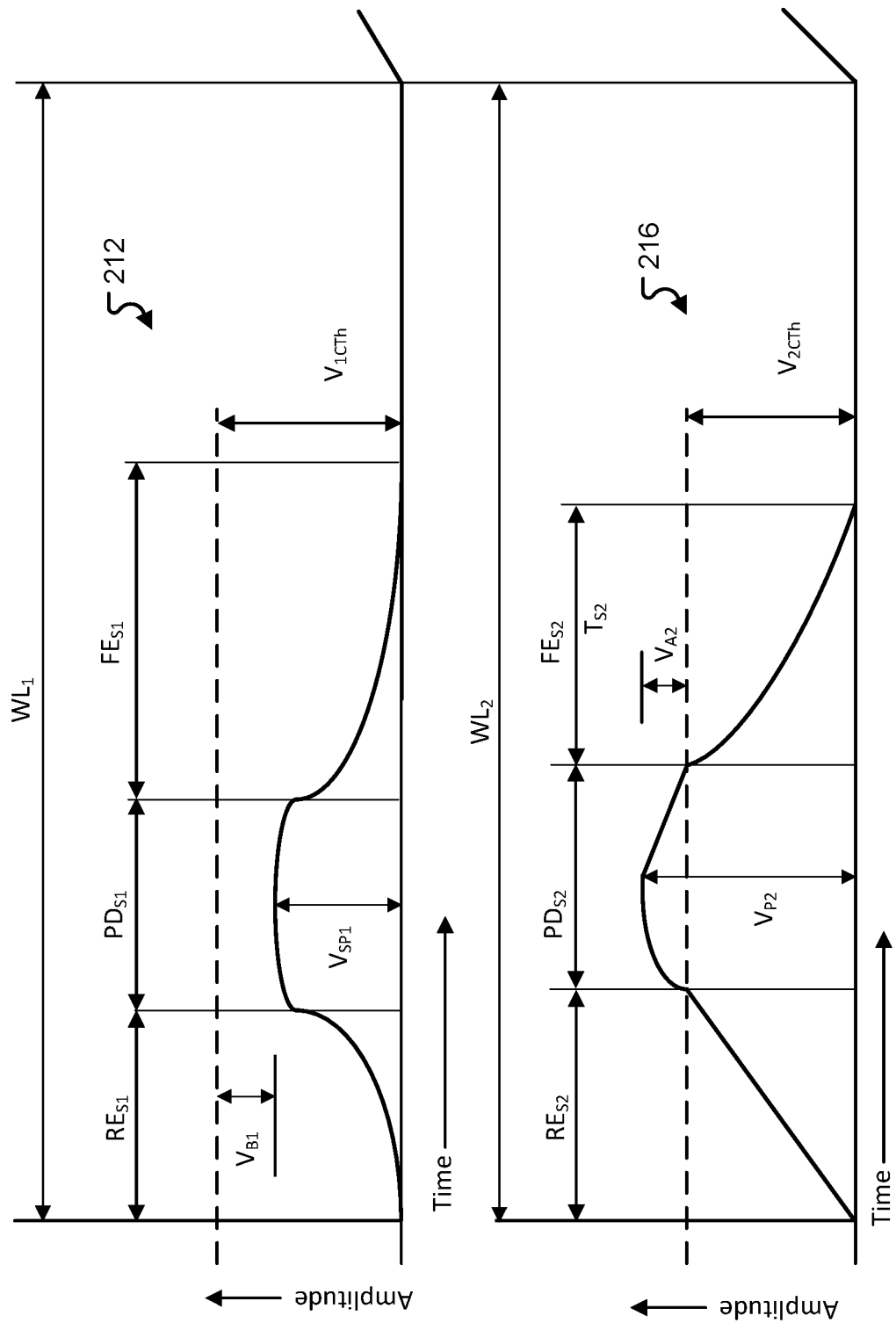

As depicted in FIGS. 2A and 2B, example waveforms of pacing signals generated by the pacing module 116 are shown in accordance with examples of the present disclosure. More specifically, a first waveform 204 may be generated as a first pacing signal having a first pacing voltage $V_{P1}$ by the pacing module 116 and may be transmitted to an electrode via one or more leads. For example, the first waveform 204 may be generated as a first pacing signal having a first pacing voltage $V_{P1}$ by the pacing module 116 and transmitted to an electrode in proximity to or otherwise associated with the right phrenic nerve 128 via the stimulation lead 124. Alternatively, the first waveform 204 may be generated as a first pacing signal having a first pacing voltage $V_{P1}$ by the pacing module 116 and transmitted to an electrode 156 in proximity to or otherwise associated with the left phrenic nerve 132 via the stimulation lead 120. The second waveform 208 may be generated as a second pacing signal having a second pacing voltage $V_{P2}$ by the pacing module 116 and transmitted to an electrode in proximity to or otherwise associated with the right phrenic nerve 128 via the stimulation lead 124. Alternatively, the second waveform 208 may be generated as a second pacing signal having a second pacing voltage $V_{P2}$ by the pacing module 116 and transmitted to an electrode 156 in proximity to or otherwise associated with the left phrenic nerve 132 via the stimulation lead 120. Accordingly, a first phrenic nerve may be stimulated by the waveform 204 while a second phrenic nerve is stimulated by a waveform 208.

As previously discussed, a first voltage amount corresponding to a first contraction threshold $V_{1CTh}$ may be determined which causes a first portion of the diaphragm 136, such as the left or right portion of the diaphragm 136 to contract in accordance with a desired tidal volume, and a second voltage amount corresponding to a second contraction threshold $V_{2CTh}$ may be separately determined to cause a second portion of the diaphragm 136, such as the other of the left or right portion of the diaphragm 136, to contract in accordance with a desired tidal volume. Thus, a voltage of a first pacing signal may be equal to $V_{P1}$ and may be less than the first contraction threshold $V_{1CTh}$ depicted in FIG. 2A and a voltage of the second pacing signal may be equal to $V_{P2}$ and may be equal or greater than the second contraction threshold $V_{2CTh}$ depicted in FIG. 2A. As further depicted in FIG. 2A, an example first waveform 204 having an amplitude equal to the first pacing voltage $V_{P1}$ is below that of the amplitude $V_{1CTh}$. That is, an amplitude, or voltage, of the first waveform 204 may be less than the first contraction threshold $V_{1CTh}$ by an amount equal to $V_{B1}$, where $V_{B1}$ is a quantity, such as a voltage, or a fraction such as a percentage of $V_{1CTh}$. As further depicted in FIG. 2A, an example second waveform 208 having an amplitude equal to the second pacing voltage $V_{P2}$ is equal to or greater than that of the second contraction threshold $V_{2CTh}$. That is, an amplitude, or voltage, of the second waveform 208 may be equal to or greater than the second contraction threshold $V_{2CTh}$ by an amount equal to $V_{A1}$, where $V_{A1}$ is a quantity, such as a voltage, or a fraction such as a percentage of $V_{2CTh}$.

The first waveform 204 may have a wavelength of $WL_1$, a rise time, or rising edge, equal to $RE_{S1}$, a pulse duration equal to $PD_{S1}$, and a falling edge, or decay time, equal to $FE_{S1}$. Similarly, the second waveform 208 may have a wavelength of $WL_2$, a rise time, or rising edge, equal to $RE_{S2}$, a pulse duration equal to $PD_{S2}$, and a falling edge, or decay time, equal to $FE_{S2}$. RES1 may be different from RES2; PDS1 may be different from PDS2, and/or FES1 may be different from FES2. Moreover, the first waveform 204, or portions of the first waveform 204, may be offset from the second waveform 208, or portions of the second waveform 208. For example, the first waveform 204 may start at a different time and may be offset by a specified amount of time from the start of the second waveform 208.

Alternatively, or in addition, a first voltage amount corresponding to a first stiffening voltage $V_{1Stiff}$ may be determined which causes a first portion of the diaphragm 136, such as the left or right portion of the diaphragm 136 to become stiff, and a second voltage amount corresponding to a second stiffening voltage $V_{2Stiff}$ may be separately determined to cause a second portion of the diaphragm 136, such as the other of the left or right portion of the diaphragm 136, to become stiff. For example, from a time $T_0$ to $T_1$, a voltage amount may be increased from 0 to $V_{1Stiff}$ such that a first portion of the diaphragm 136, such as the left or right portion of the diaphragm 136, may become stiff with little to no increase in tidal volume. From a time $T_1$ to $T_2$, a voltage amount may be increased from the stiffening voltage $V_{1Stiff}$ to the voltage $V_{P1}$ corresponding to the first pacing signal, where $V_{P1}$ is greater than the stiffening voltage $V_{1Stiff}$ and less than the first contraction threshold $V_{1CTh}$. A further depicted in FIG. 2A, a voltage of a second pacing signal may be equal to $V_{P2}$ and is greater than the second stiffening voltage $V_{2Stiff}$ and may be equal or greater than the second contraction threshold $V_{2CTh}$.

The first waveform 204 may have a wavelength of $WL_1$, a rise time, or rising edge, equal to $RE_{S1}$, a pulse duration equal to $PD_{S1}$, and a falling edge, or decay time, equal to $FE_{S1}$. Similarly, the second waveform 208 may have a wavelength of $WL_2$, a rise time, or rising edge, equal to $RE_{S2}$, a pulse duration equal to $PD_{S2}$, and a falling edge, or decay time, equal to $FE_{S2}$. RES1 may be different from RES2; PDS1 may be different from PDS2, and/or FES1 may be different from FES2. Moreover, the first waveform 204, or portions of the first waveform 204, may be offset from the second waveform 208, or portions of the second waveform 208. For example, the first waveform 204 may start at a different time and may be offset by a specified amount of time from the start of the second waveform 208.

As further depicted in FIG. 2A, a time $T_0$ to $T_1$ of the waveform 204 may be equal to a voltage rise time from a starting voltage, for example 0 volts, to the stiffening voltage $V_{1Stiff}$; a time $T_1$ to $T_2$ may be equal to a voltage rise time from the first stiffening voltage $V_{1Stiff}$ to the voltage $V_{P1}$ corresponding to the first pacing signal which is below the first contraction threshold $V_{1CTh}$; a time $T_2$ to $T_3$ may be equal to a constant, or substantially constant, pacing voltage of $V_{P1}$; a time $T_3$ to $T_4$ may be equal to a first portion of a falling edge $FE_{S1}$ corresponding to a decrease in voltage from the pacing voltage $V_{P1}$ to the stiffening voltage $V_{1Stiff}$; and a time $T_4$ to $T_5$ may be equal to a second portion of the falling edge $FE_{S1}$ corresponding to a decrease in voltage from the first stiffening voltage $V_{1Stiff}$ to an ending voltage, for example 0 volts. For the waveform 204, the amount of time (e.g., difference) between $T_1$ and $T_0$ may be greater than, less than, or equal to an amount of time (e.g., difference) between $T_5$ and $T_4$. The amount of time (e.g., difference) between $T_2$ and $T_1$ may be greater than, less than, or equal to an amount of time (e.g., difference) between $T_4$ and $T_3$. For the waveform 204, the amount of time (e.g., difference) between $T_2$ and $T_1$ may be greater than, less than, or equal to an amount of time (e.g., difference) between $T_1$ and $T_0$. For the waveform 204, the amount of time (e.g., difference) between $T_4$ and $T_3$ may be greater than, less than, or equal to an amount of time (e.g., difference) between $T_5$ and $T_4$. For the waveform 204, the amount of time (e.g., difference) between $T_3$ and $T_2$ may be greater than, less than, or equal to an amount of time (e.g., difference) between $T_5$ and $T_4$, an amount of time (e.g., difference) between $T_4$ and $T_3$, an amount of time (e.g., difference) between $T_2$ and $T_1$, and/or an amount of time (e.g., difference) between $T_1$ and $T_0$.

As further depicted in FIG. 2A, a time $T_0$ to $T_1$ of the waveform 208 may be equal to a voltage rise time from a starting voltage, for example 0 volts, to the second stiffening voltage $V_{2Stiff}$; a time $T_1$ to $T_2$ may be equal to a voltage rise time from the second stiffening voltage $V_{2Stiff}$ to the voltage $V_{P2}$ corresponding to the second pacing signal which is above the second contraction threshold $V_{2CTh}$; a time $T_2$ to $T_3$ may be equal to a constant, or substantially constant, pacing voltage of $V_{P2}$; a time $T_3$ to $T_4$ may be equal to a first portion of a falling edge $FE_{S2}$ corresponding to a decrease in voltage from the pacing voltage $V_{P2}$ to the stiffening voltage $V_{2Stiff}$; and a time $T_4$ to $T_5$ may be equal to a second portion of the falling edge $FE_{S2}$ corresponding to a decrease in voltage from the second stiffening voltage $V_{2Stiff}$ to an ending voltage, for example 0 volts. For the waveform 208, the amount of time (e.g., difference) between $T_1$ and $T_0$ may be greater than, less than, or equal to an amount of time (e.g., difference) between $T_5$ and $T_4$. The amount of time (e.g., difference) between $T_2$ and $T_1$ may be greater than, less than, or equal to an amount of time (e.g., difference) between $T_4$ and $T_3$. For the waveform 208, the amount of time (e.g., difference) between $T_2$ and $T_1$ may be greater than, less than, or equal to an amount of time (e.g., difference) between $T_1$ and $T_0$. For the waveform 208, the amount of time (e.g., difference) between $T_4$ and $T_3$ may be greater than, less than, or equal to an amount of time (e.g., difference) between $T_5$ and $T_4$. For the waveform 208, the amount of time (e.g., difference) between $T_3$ and $T_2$ may be greater than, less than, or equal to an amount of time (e.g., difference) between $T_5$ and $T_4$, an amount of time (e.g., difference) between $T_4$ and $T_3$, an amount of time (e.g., difference) between $T_2$ and $T_1$, and/or an amount of time (e.g., difference) between $T_1$ and $T_0$.

FIG. 2B depicts additional examples of waveforms generated by the pacing module 116 in accordance with examples of the present disclosure. More specifically, a first waveform 212 may be different from a second waveform 216. For example, a shape of a first waveform 212 may be different from a shape of the second waveform 216. An amplitude, or voltage, of the waveform utilized for pacing the right side or left side of the diaphragm 136 is less than an amplitude or voltage of $V_{1CTh}$ by an amount equal to VB, where $V_{B1}$ is a quantity, such as a voltage, or a fraction such as a percentage of $V_{1CTh}$. An amplitude, or voltage, of the waveform utilized for pacing the other of the left side or right side of the diaphragm 136 is equal or greater than an amplitude or voltage of $V_{2CTh}$ by an amount equal to $V_{A2}$, where $V_{A2}$ is a quantity, such as voltage, or a fraction such as a percentage of $V_{2CTh}$.

Figure 3:
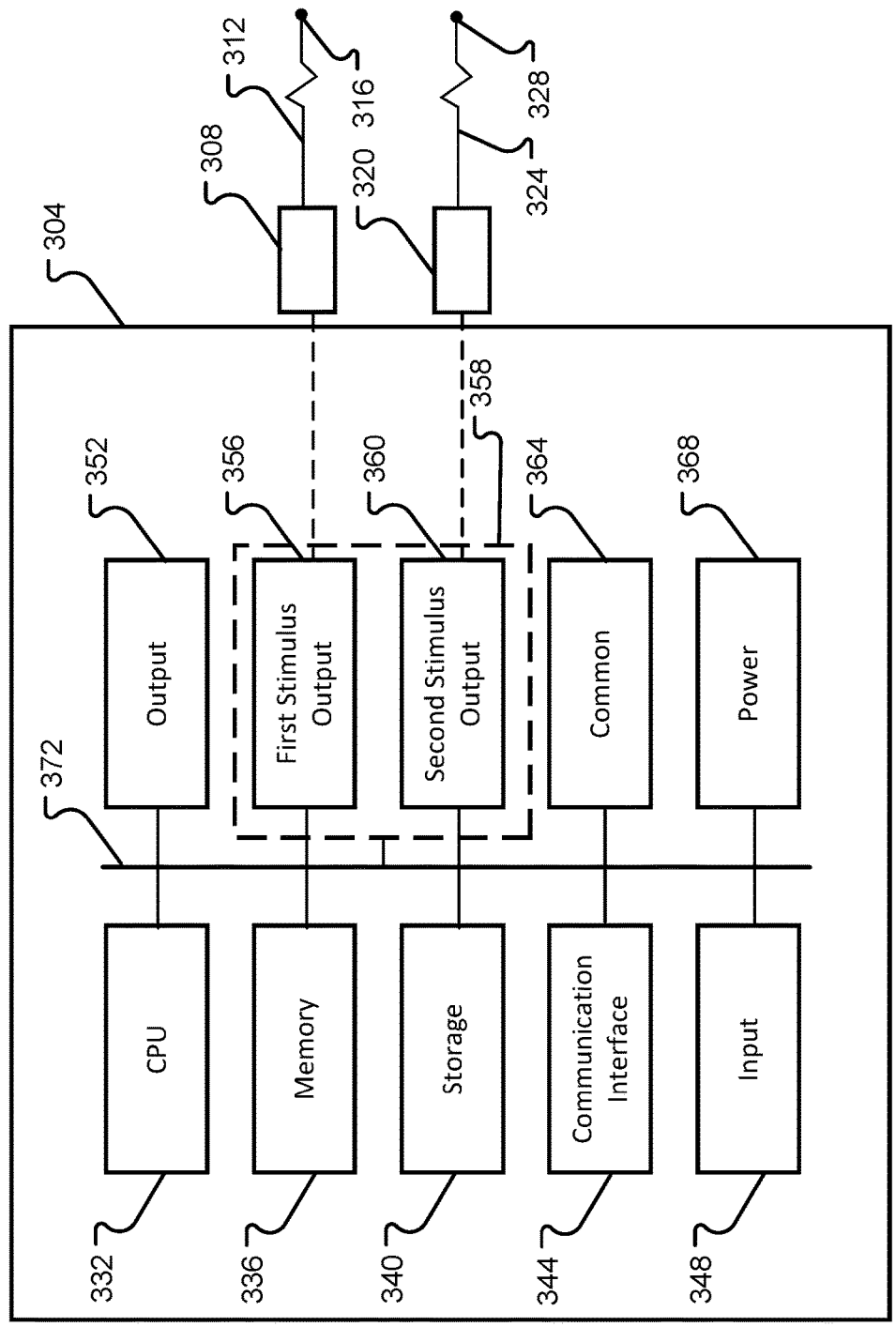
FIG. 3 illustrates an example block diagram including additional details of a pacing module 304.

FIG. 3 depicts a block diagram of a pacing module 304 in accordance with examples of the present disclosure. The pacing module 304 may include a CPU 332, memory 336, storage 340, communication interface 344, input 348, output 352, first stimulus output 356, second stimulus output 360, signal generator 358, common 364, and a power source 368 coupled to one another via one or more power and/or communication buses 372. The pacing module 304 may be the same as or similar to the pacing module 116 previously described. More specifically, the pacing module 304 may be configured to receive a first coupling connector 308 coupling a first lead 312 to a first electrode 316, where the first lead 312 may be the same as or similar to the stimulation lead 120 previously described and the first electrode 316 may be same as or similar to the first electrode described with respect to FIG. 1. The pacing module 304 may be configured to receive a second coupling connector 320 coupling a second lead 324 to a second electrode 328, where the second lead 324 may be the same as or similar to the stimulation lead 120 previously described and the second electrode 328 may be same as or similar to the electrode 156 previously described.

The first coupling connector 308 may be configured to interface with the first stimulus output 356 to receive a first stimulus, such as a first pacing signal having a first pacing voltage, and the second coupling connector 320 may be configured to interface with the second stimulus output 360 to receive a second stimulus, such as a second pacing signal having a second pacing voltage. The first stimulus output 356 and the second stimulus output 360 may be generated from a signal generator 358 for example, where the signal generator 358 may be configured to generate one or more stimuli, or waveforms, causing a first portion of a diaphragm 136 to stiffen and a second portion of the diaphragm to contract. For example, the signal generator 358 may be configured to generate stimuli and/or waveforms similar to or the same as those waveforms described with respect to FIGS. 2A-2B.

The CPU 332 may be capable of executing program instructions and may be configured to cause one or more of the first stimulus output 356, signal generator 358, and/or second stimulus output 360 to generate a first and/or second stimulus output as previously described. The CPU 332 may include any general-purpose programmable processor or controller for executing application programming. Alternatively, or in addition, the CPU 332 may comprise an application specific integrated circuit (ASIC). The CPU 332 generally functions to execute programming code that implements various functions performed by the pacing module 304 in accordance with at least some examples of the present disclosure.

As previously discussed, the pacing module 304 may additionally include memory 336. The memory 336 may be used in connection with the execution of programming instructions by the CPU 332, and for the temporary or long-term storage of data and/or program instructions. For example, the CPU 332, in conjunction with the memory 336 of the pacing module 304, may operate to cause one or more of the first stimulus output 356, signal generator 358, and/or second stimulus output 360 to generate a first and/or second pacing signal output as previously described.

The memory 336 may include solid-state memory that is resident, removable and/or remote in nature, such as DRAM and SDRAM. Moreover, the memory 336 may include a plurality of discrete components of different types and/or a plurality of logical partitions. In accordance with still other examples, the memory 336 includes a non-transitory computer readable storage medium. Such a medium may take many forms, including but not limited to, non-volatile media, volatile media, and transmission media.

The pacing module 304 may be coupled to or otherwise include an input 348 and/or an output 352 that allows a user and/or a ventilator chassis 108 to interact with the pacing module 304, to operate the pacing module 304, and/or to interact with a feature, function, and/or application of the pacing module 304. For example, a user of the pacing module 304 may determine an optimal configuration, initiate a procedure and/or process for determining a pacing signal and/or voltages of the pacing signals for a right and/or left portion of a patient's diaphragm 136, and/or initiate a procedure and/or process for causing the first stimulus output 356 and/or second stimulus output 360 to output a stimulus, or pacing signal having a voltage, to one or more of the first electrode 316 and/or second electrode 328. Moreover, a user may interact with the input 348 and/or output 352 to configure one or more parameters of the pacing module 304 and/or the ventilator chassis 108, operate or otherwise interact with one or more applications running on the pacing module 304 and/or ventilator chassis 108, and configure one or more patient profiles for example. Examples of input 348 include but are not limited to a keypad, a touch screen, a microphone, and a pointing device. Examples of an output 352 include but are not limited to a display which may be a touch screen display, a speaker, and one or more haptic output devices for example. Additional details of a user interface associated with the input 348 and/or output 352 are provided with respect to FIG. 7.

The pacing module 304 may be equipped with a communication interface 344. The communication interface 344 may include a transceiver capable of supporting voice, multimedia and/or data transfers over a communications network. Alternatively, or in addition, the communication interface 344 may include a Wi-Fi, BLUETOOTH™, infrared, NFC or other wireless communications link. The communication interface 344 may be associated with one or more shared or dedicated antennas. The type of medium used by the pacing module 304 to communicate with other devices may depend upon the communication applications availability on the pacing module 304 and/or the availability of a communication medium.

The pacing module 304 may include a power source 368; the power source 368 may include, but is not limited to a battery, an AC to DC converter, power control logic, and/or ports for interconnecting the pacing module 304 to an external source of power. As previously discussed, the pacing module 304 may include a first stimulus output 356 and/or a second stimulus output 360. In some examples, a ground, or common connection 364 may be desired to ensure the patient and the pacing module 304 are operating with respect to a same reference point in an electrical circuit from which voltages are measured.

Figure 4:
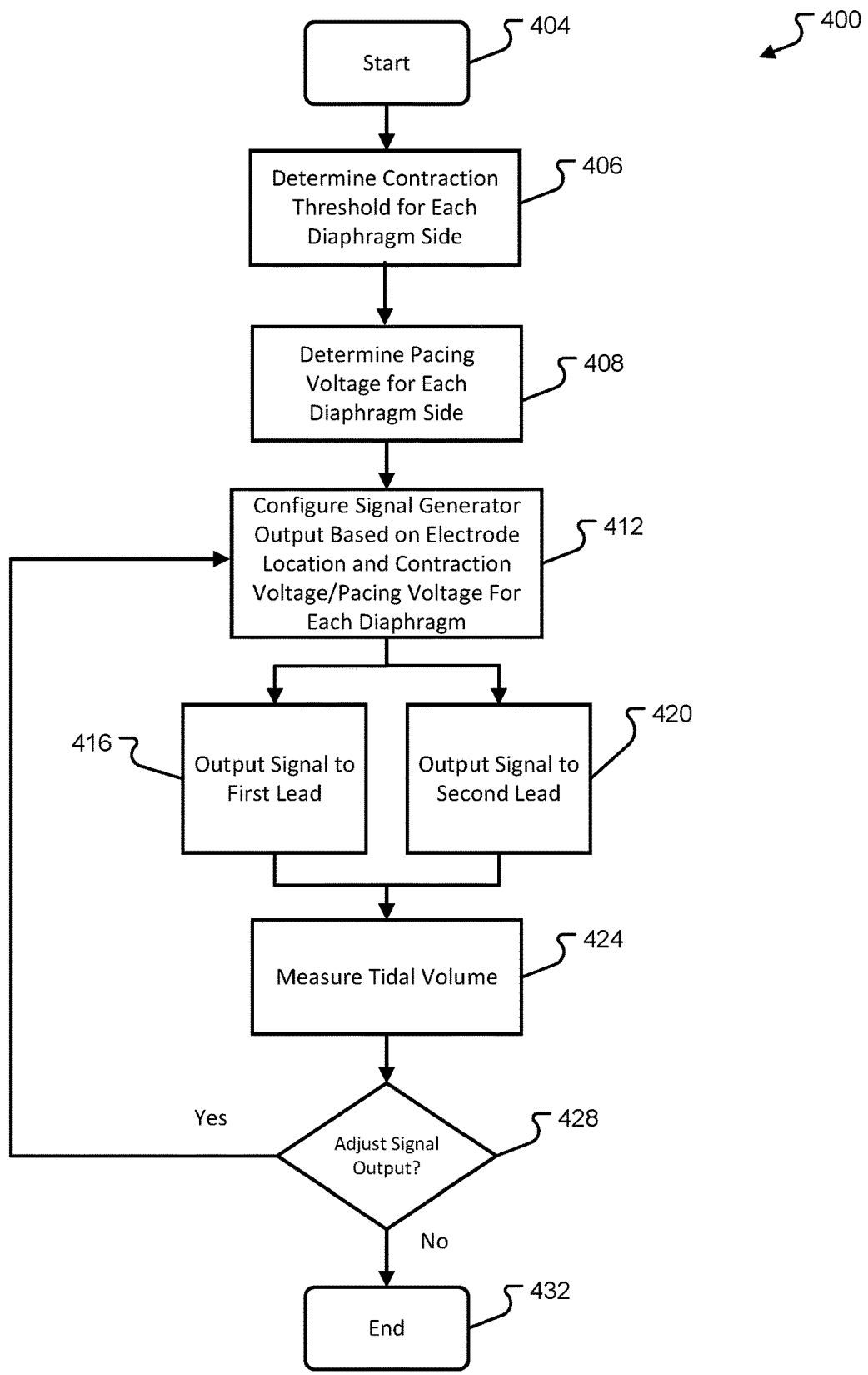
FIG. 4 provides a flow diagram for a method of providing phrenic nerve stimulation system.

Referring now to FIG. 4, a method 400 of performing phrenic nerve pacing in accordance with examples of the present disclosure is provided. The method 400 is in examples, performed by a device, such as a pacing module 304 and/or ventilator chassis 108. More specifically, one or more hardware and software components may be involved in performing the method 400. In one example, one or more of the previously described modules and/or devices perform one or more of the steps of the method 400. The method 400 may be executed as a set of computer-executable instructions executed by a pacing module 304 encoded or stored on a computer-readable medium. Hereinafter, the method 400 shall be explained with reference to systems, components, modules, software, etc. described with FIGS. 1-3.

The method 400 may continuously flow in a loop, flow according to a timed event, or flow according to a change in an operating or status parameter. The method 400 may be initiated at step 404 where a patient may be undergoing positive pressure ventilation with a ventilator chassis 108. For example, a patient may be intubated with a breathing tube, also referred to as an endotracheal tube, which is inserted in the patient's trachea or windpipe through the mouth or nose. In other examples, a patient may require assistance with breathing patterns and/or breathing rhythms throughout the day and/or night and may therefore undergo breathing treatment with phrenic nerve pacing. Accordingly, the patient undergoing phrenic nerve pacing will have a first electrode inserted, implanted or otherwise brought into proximity to or otherwise in communication with a first phrenic nerve and a second electrode inserted, implanted or otherwise brought into proximity to or otherwise in communication with a second phrenic nerve. For example, the first electrode 316 may be in proximity to a right phrenic nerve 128 and the second electrode 328 may be in proximity to a left phrenic nerve 132. Each of the first electrode 316 and the second electrode 328 may be placed during a surgical session.

At step 406, a contraction threshold for each side of a patient's diaphragm may be determined. For example, a first contraction threshold causing the right side of the patient's diaphragm 136 to contract may be determined and a second contraction threshold causing the left side of the patient's diaphragm 136 to contract may be determined. Additional details with respect to determining contraction thresholds and voltages of the contraction thresholds that cause the different sides of the patient's diaphragm to contract are provided with respect to FIG. 5.

At step 408, a pacing voltage for each side of a patient's diaphragm may be determined. In some examples, a pacing voltage for the side of the patient's diaphragm having the highest contraction threshold may be configured to be below the contraction threshold (the highest contraction threshold) and a pacing voltage for the side of the patient's diaphragm having the lowest contraction threshold may be configured to be equal to or greater than the contraction threshold (the lowest contraction threshold), where the contraction threshold for the right side of the diaphragm may be different from the contraction threshold for the left side of the diaphragm.

Figure 6:
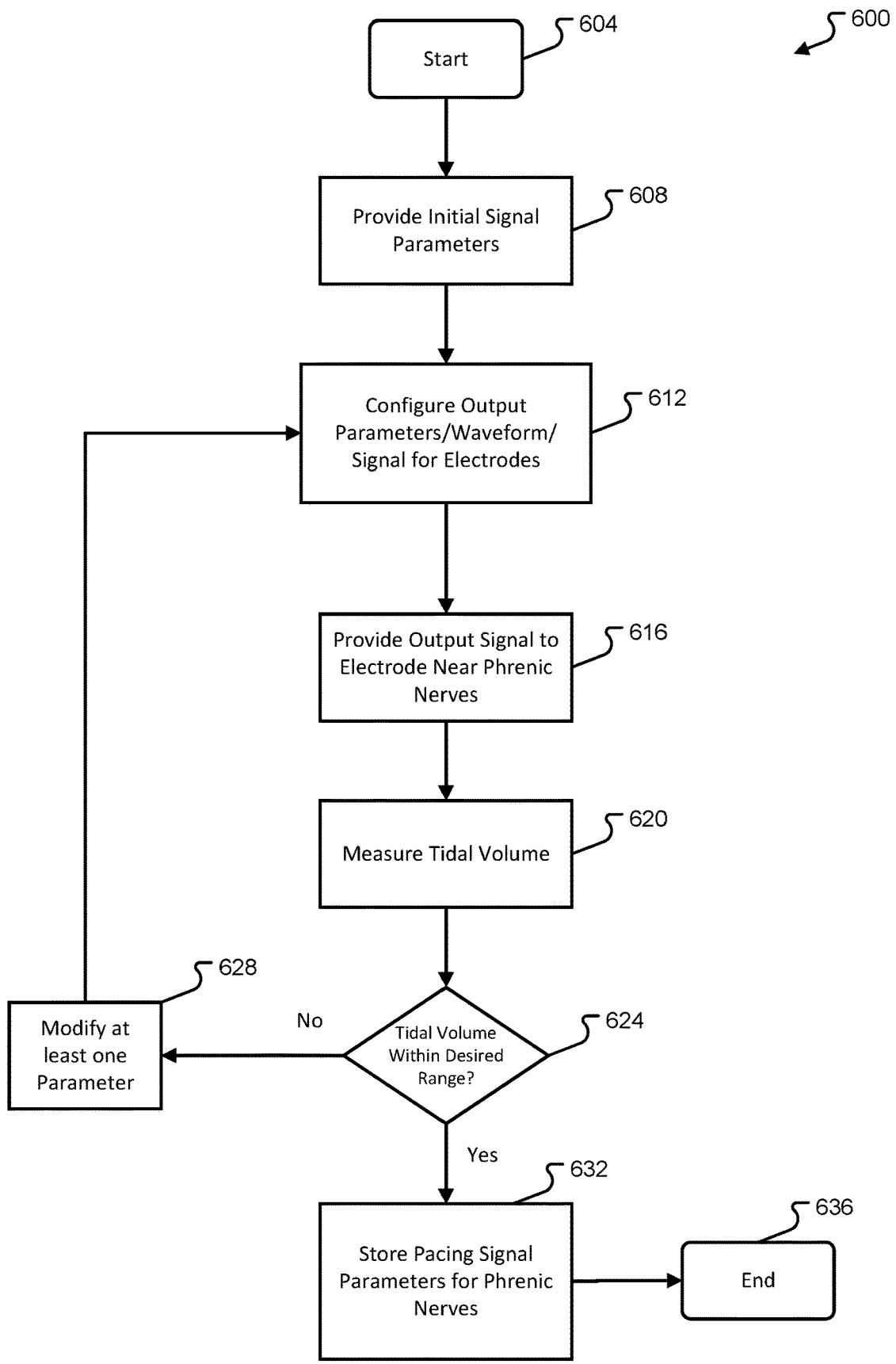
FIG. 6 provides a flow diagram for generating pacing signals having pacing voltages based on output signal parameters.

A pacing signal having a pacing voltage that causes the right portion of the patient's diaphragm 136 to stiffen may be determined and a pacing signal having a pacing voltage causing the left portion of the patient's diaphragm 136 to contract may be determined. Alternatively, a pacing signal having a pacing voltage that causes the right portion of the patient's diaphragm 136 to contract may be determined and a pacing signal having a pacing voltage causing the left portion of the patient's diaphragm 136 to stiffen may be determined. Additional details with respect to determining optimal pacing signals and pacing voltages that cause portions of a patient's diaphragm to stiffen or contract are provided with respect to FIG. 6.

At step 412, an output of a signal generator, for example the signal generator 358, may be configured based on the determined pacing signals and cause the first stimulus output 356 and the second stimulus output 360 to each provide a pacing signal having a pacing voltage to the respective electrodes via respective leads. In accordance with examples of the present disclosure, the phrenic nerve associated with a side of the diaphragm having a largest contraction threshold may be paced with a pacing signal having a pacing voltage that is below the first contraction threshold. For example, a first waveform 204 of FIG. 2A may be generated by the first stimulus output 356 and provided to an electrode associated with the phrenic nerve for a side of the diaphragm having a largest contraction threshold. In accordance with examples of the present disclosure, the phrenic nerve associated with a side of the diaphragm having the smaller contraction threshold may be paced with a pacing signal having a pacing voltage that is equal to or greater than the second contraction threshold thereby causing the side of the diaphragm to contract. For example, a second waveform 208 of FIG. 2A may be generated by the second stimulus output 360 and provided to an electrode associated with the phrenic nerve for the side of the diaphragm having the smallest contraction threshold.

Alternatively, and in accordance with examples of the present disclosure, the phrenic nerve associated with a side of the diaphragm having the smallest contraction threshold may be paced with a pacing signal having a pacing voltage that is below the first contraction threshold. For example, a first waveform 204 of FIG. 2A may be generated by the first stimulus output 356 and provided to an electrode associated with the phrenic nerve for the side of the diaphragm having the smallest contraction threshold. In accordance with examples of the present disclosure, the phrenic nerve associated with the side of the diaphragm having the largest contraction threshold may be paced with a pacing signal having a pacing voltage that is equal to or greater than the second contraction threshold. For example, a second waveform 208 of FIG. 2A may be generated by the second stimulus output 360 and provided to an electrode associated with the phrenic nerve for the side of the diaphragm having the largest contraction threshold.

At steps 416 and 420, the respective pacing signals generated by the signal generator 358 (or the first stimulus output 356 and second stimulus output 360) are provided to respective first and second leads, where the first lead may be associated with a first electrode in proximity to a first phrenic nerve and the second lead may be associated with a second electrode in proximity to a second phrenic nerve. The first stimulus output 356 may provide a first pacing signal having the first pacing voltage to the stimulation lead 120 associated with an electrode in proximity to the right phrenic nerve 128. Alternatively, or in addition, the second stimulus output 360 may provide the first pacing signal having the first pacing voltage to the stimulation lead 124 associated with an electrode 156 in proximity to the left phrenic nerve 132.

At step 424, a tidal volume of the patient may be measured for a specified duration of time corresponding to one breathing cycle, such as a duration of one waveform $WL_1$ and/or $WL_2$. While FIG. 4 indicates that the tidal volume may be measured, other parameters associated with ventilation may be measured. For example, parameters including, but not limited to end-tidal carbon dioxide ($ETCO_2$), maximum partial pressure of CO2 at the end of breath (PETCO2), partial pressure of CO2 in the alveoli, and Work of Breath (WOB), partial atrial carbon dioxide or any other mechanisms—indirect or direct indicate a rise in the carbon dioxide level may be measured. Based on one or more of these parameter measurements for example, a determination may be made at step 428 as to whether the pacing signals and/or pacing voltages for the left and/or right phrenic nerves should be adjusted. If the pacing signals and/or pacing voltages should be adjusted, the method 400 may flow to step 412, where the signal generator 358 (first stimulus output 356 and/or second stimulus output 360) may adjust one or more pacing signals to achieve a desired tidal volume and/or a desired parameter quantity. The method 400 may end at step 432.

Figure 5:
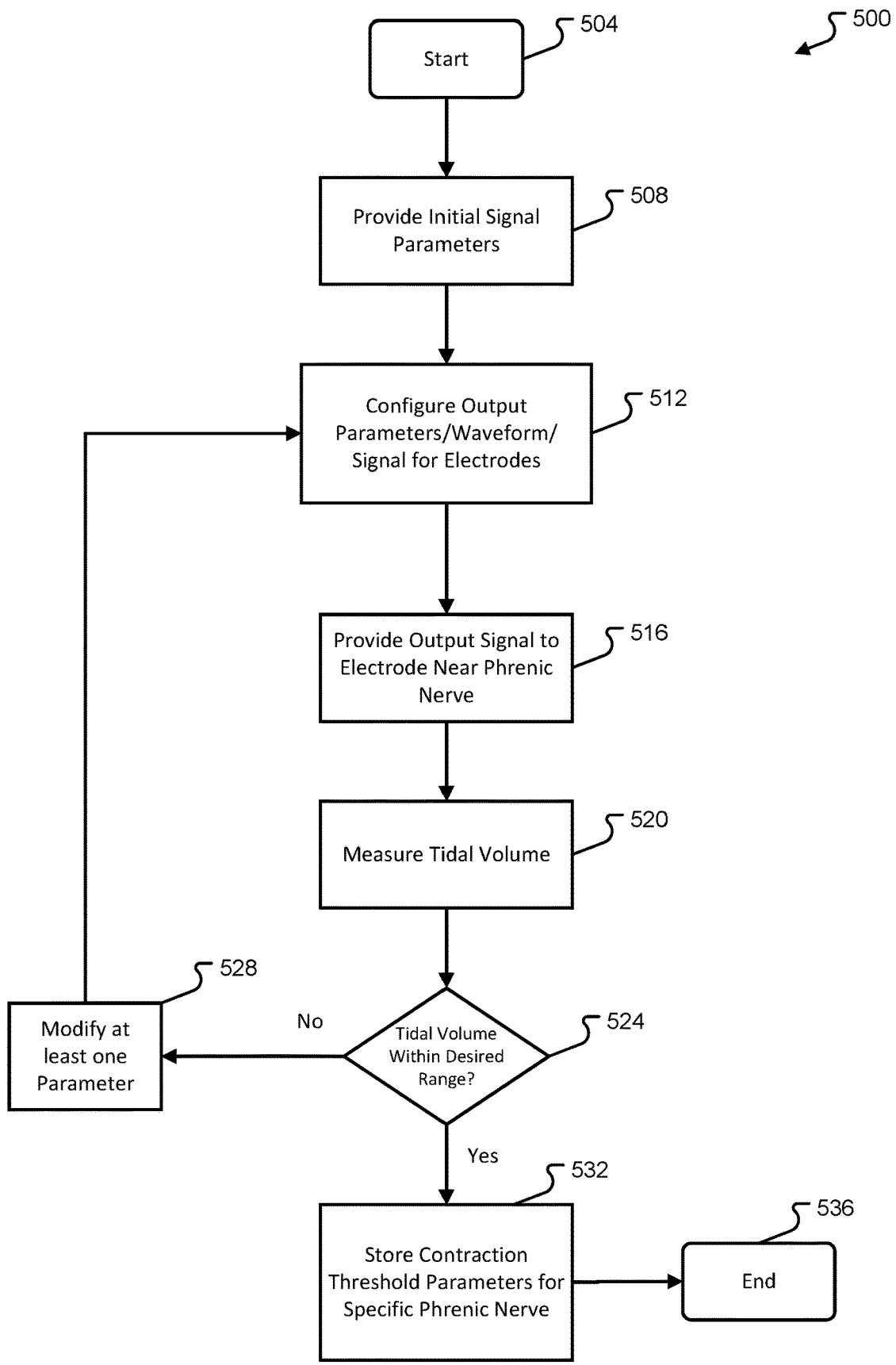
FIG. 5 provides a flow diagram for a method of determining threshold pacing voltages for use by the phrenic nerve stimulation system.

Referring now to FIG. 5, a method 500 of determining first and second contraction thresholds for a given tidal volume is provided in accordance with examples of the present disclosure. The method 500 is in examples, performed by a device, such as a pacing module 304 and/or ventilator chassis 108. More specifically, one or more hardware and software components may be involved in performing the method 500. In one example, one or more of the previously described modules and/or devices perform one or more of the steps of the method 500. The method 500 may be executed as a set of computer-executable instructions executed by a pacing module 304 encoded or stored on a computer-readable medium. Hereinafter, the method 500 shall be explained with reference to systems, components, modules, software, etc. described with FIGS. 1-4.

The method 500 may continuously flow in a loop, flow according to a timed event, or flow according to a change in an operating or status parameter. The method 500 may be initiated at step 504 where a patient may be undergoing positive pressure ventilation with a ventilator chassis 108. Alternatively, the patient may require assistance with breathing patterns and/or breathing rhythms throughout the day and/or night and may therefore undergo breathing treatment with phrenic nerve pacing. Once electrodes have been placed in proximity to a patient's left and right phrenic nerve, and prior to utilizing a phrenic pacing system to assist a patient with breathing, a contraction threshold associated with each side of the patient's diaphragm is determined. The method 500 may start at step 504 and flow to step 508, where initial signal parameters to be applied to a phrenic nerve of one side of the patient's diaphragm are obtained. In at least one example, the initial signal parameters may be provided from or otherwise obtained from one or more storage locations of the pacing module 304, for example the memory 336 and/or the storage 340.

At step 512, the CPU 332 may configure or generate one or more parameters to cause a signal to be output and applied to a phrenic nerve of a patient. For example, one or more of a pulse duration, rise time, fall time, period, frequency, and/or duty cycle may be generated, or specified, at the CPU 332 and provided to the signal generator 358 such that one or more of the first stimulus output 356 and/or second stimulus output 360 may output an electrical pulse signal. At step 516, the electrical pulse signal may be provided by the first stimulus output 356, signal generator 358, or the second stimulus output 360 to an electrode near a phrenic nerve of the patient, and thereby cause a side of the diaphragm associated with the stimulated phrenic nerve to contract. The contraction of the diaphragm muscles cause the chest cavity to expand such that air, or gas, is inhaled. When the falling edge of the electrical pulse reaches zero, the phrenic nerve may no longer be stimulated by the pacing module 304 and the diaphragm muscle may relax, thereby shrinking the chest cavity and forcing the air, or gas, out of the lungs. A tidal volume may be measured based on the inspiration and/or exhalation caused by the contraction of the side of the diaphragm stimulated by the phrenic nerve; in some instance, the tidal volume may be received at the pacing module 304 directly from a spirometer itself. Accordingly, if the tidal volume is within a given range, a contraction threshold for the phrenic nerve may be stored within the storage 340 and/or the memory 336 at step 532 and the method 500 may end at step 536. If, however, the measured tidal volume is not within a desired range, then the method 500 may proceed to step 528 where at least one parameter, such as a voltage, pulse frequency, pulse duration, duty cycle, pulse shape, rising edge, and/or falling edge may be adjusted. The method 500 may then proceed back to step 512 where the steps 512 through 524 may be repeated until a measured tidal volume is within a desired range.

The method 500 may be repeated for each phrenic nerve of a patient. Moreover, as lung compliance impacts at least an amplitude of an electrical pulse needed to achieve a desired contraction and corresponding tidal volume, the method 500 is generally dependent upon the patient.

Referring now to NG. 6, a method 600 of varying signal parameters, such as voltages and/or waveforms, to determine optimal signal voltages of first and second pacing signals for a desired tidal volume is provided in accordance with examples of the present disclosure. An optimal signal voltage for a first pacing signal, $V_{P1}$ for example, may be greater than the first stiffening voltage $V_{1Stiff}$ but less than the first contraction threshold $V_{1CTh}$. An optimal signal voltage for a second pacing signal, $V_{P2}$ for example, may be greater than the second stiffening voltage $V_{2Stiff}$ and equal to or greater than the second contraction threshold $V_{2CTh}$. The method 600 is in examples, performed by a device, such as a pacing module 304 and/or ventilator chassis 108. More specifically, one or more hardware and software components may be involved in performing the method 600. In one example, one or more of the previously described modules and/or devices perform one or more of the steps of the method 600. The method 600 may be executed as a set of computer-executable instructions executed by a pacing module 304 encoded or stored on a computer-readable medium. Hereinafter, the method 600 shall be explained with reference to systems, components, modules, software, etc. described with FIGS. 1-5.

The method 600 may continuously flow in a loop, flow according to a timed event, or flow according to a change in an operating or status parameter. The method 600 may be initiated at step 604 where a patient may be undergoing positive pressure ventilation with a ventilator chassis 108. Alternatively, the patient may require assistance with breathing patterns and/or breathing rhythms throughout the day and/or night and may therefore undergo breathing treatment with phrenic nerve pacing. The method 600 may be initiated at the conclusion of method 500; that is, whereas the method 500 may identify a contraction threshold for the left diaphragm portion and a contraction threshold for the right diaphragm portion, the method 600 may identify optimal signal voltages for each of the first and second pacing signals to achieve a desired or target tidal volume. The method 600 may start at step 604 and flow to step 608, where initial signal parameters to be applied to the right and left phrenic nerves are obtained. The initial signal parameters may correspond to a contraction threshold for the right diaphragm side and a contraction threshold for a left diaphragm side. In at least one example, the initial signal parameters may be provided from or otherwise obtained from one or more storage locations of the pacing module 304, for example the memory 336 and/or the storage 340.

At step 612, the CPU 332 may configure or generate one or more parameters to cause a signal to be output and applied to the right and left phrenic nerves of a patient. For example, one or more of a pulse duration, rise time, fall time, period, frequency, and/or duty cycle may be generated, or specified, at the CPU 332 and provided to the signal generator 358 such that one or more of the first stimulus output 356 and/or second stimulus output 360 output an electrical pulse signal. In a first example, a voltage for a first signal to be applied to the side of the diaphragm having the highest contraction threshold may be incrementally adjusted over a range of voltages spanning from just below the contraction threshold to zero volts. For example, a first signal for a first breath cycle may be equal to the contraction threshold minus 0.1 volts and/or a first signal for a second breath cycle may be equal to the contraction threshold minus 0.2 volts. In a same example, a voltage for a second signal to be applied to the side of the diaphragm having the lowest contraction threshold may be incrementally adjusted over a range of voltages spanning from a voltage value equal to the contraction threshold to a voltage value equal to the contraction threshold plus 0.5 volts. For example, a second signal for a first breath cycle may be equal to the contraction threshold and/or a second signal for a second breath cycle may be equal to the contraction threshold plus 0.1 volts. It should be appreciated that the range of voltages are provided for example purposes and other ranges may exist.

At step 616, the first and second signals may be provided by the first stimulus output 356, signal generator 358, or the second stimulus output 360 to respective electrodes near respective phrenic nerves of the patient, and thereby cause a side of the diaphragm associated with a first stimulated phrenic nerve to stiffen and a side of the diaphragm associated with a second phrenic nerve to contract. The stiffening of the diaphragm muscles of the side of the diaphragm associated with a first stimulated phrenic nerve and the contraction of the diaphragm muscles of the side of the diaphragm associated with the second stimulated phrenic nerve causes the chest cavity to expand such that air, or gas, is inhaled. When the phrenic nerves are no longer stimulated, such as when the each of the waveforms is at a zero voltage, the diaphragm muscle may relax, thereby shrinking the chest cavity and forcing the air, or gas, out of the lungs. A tidal volume may be measured for each breath cycle based on the inspiration and/or exhalation caused by the stimulated phrenic nerves; in some instance, the tidal volume may be received at the pacing module 304 directly from a spirometer. Accordingly, if the tidal volume is within a given range, the pacing signal parameters for the right and left phrenic nerves may be stored as respective pacing signals within the storage 340 and/or the memory 336 at step 632 and the method 600 may end at step 636. If, however, the measured tidal volume is not within a desired range, then the method 600 may proceed to step 628 where at least one parameter, such as a voltage, pulse frequency, pulse duration, duty cycle, pulse shape, rising edge, and/or falling edge may be adjusted. For example, a first signal for a second breath cycle may be adjusted to equal the contraction threshold minus 0.2 volts while the voltage for a second signal for the may be equal to the contraction threshold. The method 600 may then proceed back to step 612 where the steps 612 through 624 may be repeated until a measured tidal volume is within a desired range.

Figure 7:
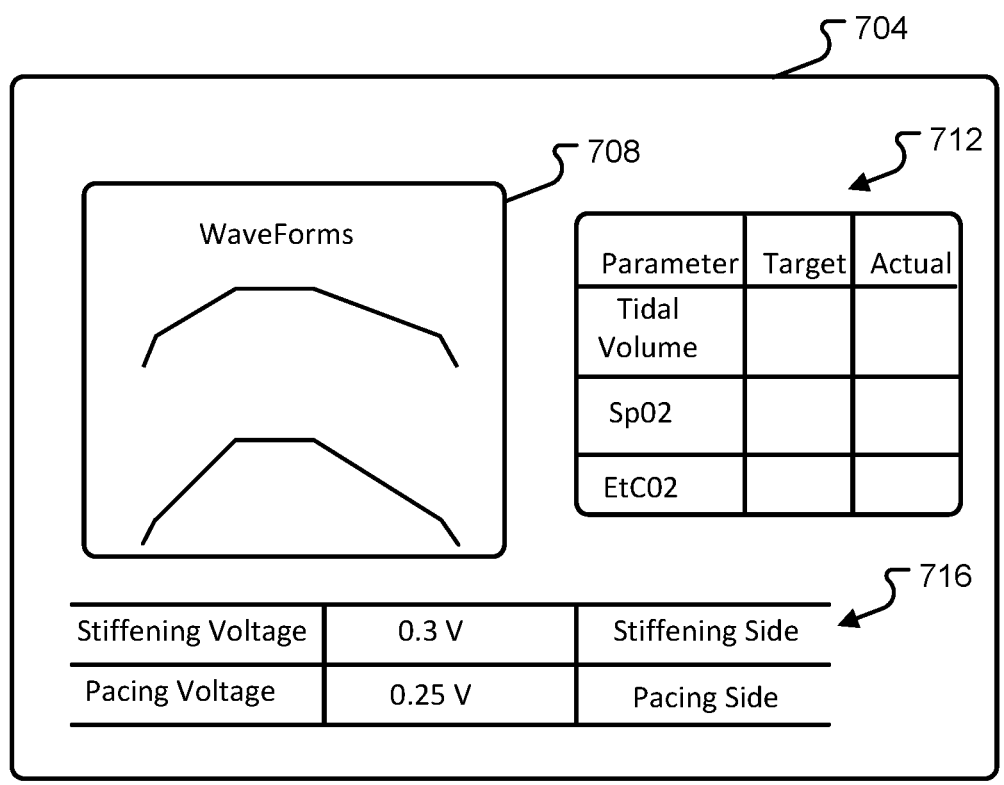
FIG. 7 illustrates an example user interface depicting phrenic nerve stimulation system information.

FIG. 7 is a block diagram depicting an example user interface 704 associated with a ventilator chassis 108 and/or pacing module 116 in accordance with examples of the present disclosure. More specifically, the user interface 704 may be displayed as an output, for example output 352 of the pacing module 304. The user interface 704 may display information associated with phrenic nerve stimulation; that is the user interface 704 may display example waveforms 708, one or more parameters 712 of a patient's breathing patterns, and phrenic nerve stimulation information 716. The one or more parameters 712 may display, but is not limited to, tidal volume information and gas exchanging information. The phrenic nerve stimulation information 716 may display a stiffening voltage, or amplitude, for the side of the diaphragm being paced with a pacing signal having a voltage below the contraction threshold. The phrenic nerve stimulation information 716 may also indicate which side is being stiffened (e.g., side having a highest contraction threshold), indicate which side is being paced (e.g., side having the lowest contraction threshold), as well as display information about the stimulus being applied to one or more phrenic nerves, such as an amplitude, frequency, etc. In some examples, a side of the diaphragm that is being paced below the contraction threshold (e.g., the stiffening side) may alternate with the side that is being paced above the contraction threshold (e.g., pacing side). For example, after a first duration of time and/or breathes, the pacing side may become the stiffening side and the stiffening side may become the pacing side; this duration of time may correspond to seconds, minutes, hours; days, weeks and/or a number of breathes.

Figure 8:
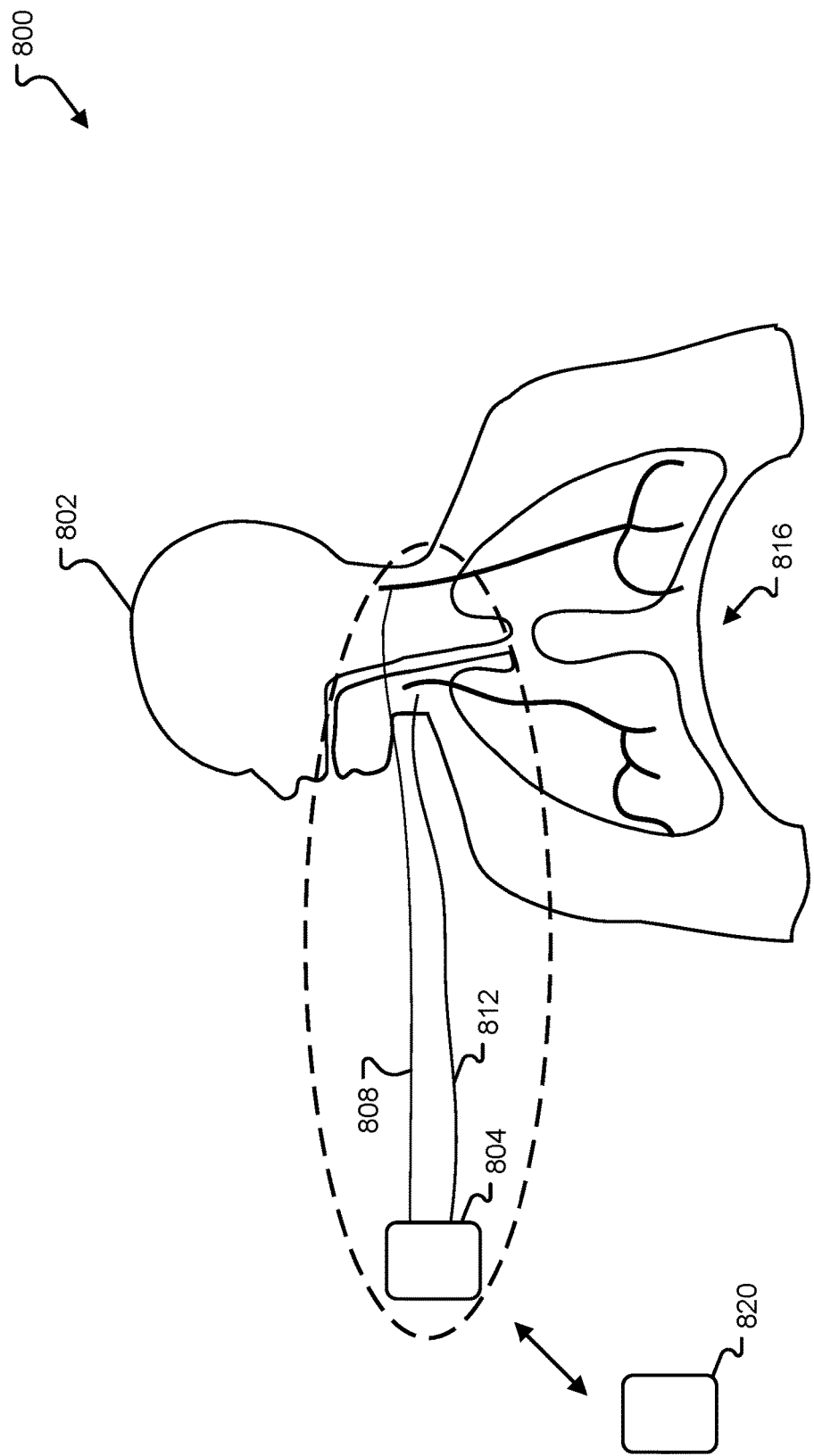
FIG. 8 illustrates a block diagram of a phrenic nerve stimulation system.

FIG. 8 is a block diagram depicting a phrenic nerve stimulation system 800 that achieves a smooth breathing pattern with a desired tidal volume. Unlike the phrenic nerve stimulation system 100, the phrenic nerve stimulation system 800 may not include a ventilator chassis but otherwise provides breathing support for a patient 802 via a pacing module 804 which may include a portion implanted within the patient 802. For example, the pacing module 804, which may be the same as or similar to the pacing module 116 and/or the pacing module 304, and the first and second stimulation leads 808 and 812, may be implanted within the patient 802 such that continuous phrenic nerve stimulation treatments may be applied to the patient 802. The pacing module 116 may be coupled to stimulation leads 120 and 124; electrodes may be coupled to distal portions of each of the stimulation leads 120 and 124 such that the electrodes may be placed in proximity to the phrenic nerve 128 and/or phrenic nerve 132. Further, the pacing module 804 may wirelessly communicate with a reader/writer 820 which may configure or otherwise program the pacing module 804 to provide a desired pacing signal having a desired pacing voltage to each of the patient's left and right phrenic nerves. Accordingly, in instances where breathing patterns may need to be regulated, the patient 802 may utilize the phrenic nerve stimulation system 800.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method for providing bilateral phrenic nerve pacing, the method comprising:
    determining a first contraction threshold at which a first portion of diaphragm muscles contract, in response to stimulating a first phrenic nerve, to draw a first desired tidal volume into lungs of a patient;
    determining a second contraction threshold at which a second portion of the diaphragm muscles contract, in response to stimulating a second phrenic nerve, to draw a second desired tidal volume into the lungs of the patient;
    generating a first pacing signal having a first amplitude less than the first contraction threshold;
    delivering the first pacing signal in proximity to the first phrenic nerve, thereby stiffening the first portion of the diaphragm muscles;
    generating a second pacing signal having a second amplitude equal to or greater than the second contraction threshold, the second amplitude being different from the first amplitude; and
    while delivering the first pacing signal, delivering the second pacing signal in proximity to the second phrenic nerve, thereby contracting the second portion of the diaphragm muscles.

2. The method of claim 1, wherein the first contraction threshold is equal to the second contraction threshold.

3. The method of claim 1, wherein the first amplitude is delivered to the first phrenic nerve but not the second phrenic nerve.

4. The method of claim 1, further comprising:
    modifying a first output signal having the first contraction threshold until a measured tidal volume is within a first desired range; and
    modifying a second output signal having the second contraction threshold until a measured tidal volume is within a second desired range.

5. The method of claim 1, further comprising:
    modifying a parameter of the first pacing signal, wherein the parameter is one of: a frequency, a pulse duration, or a pulse shape.

6. The method of claim 1, wherein the first amplitude of the first pacing signal is a voltage greater than zero.

7. The method of claim 1, further comprising:
    providing positive pressure ventilation to the patient while delivering the first pacing signal and the second pacing signal.

8. A ventilator system comprising:
    a phrenic nerve stimulator performing a set of operations comprising:
        determining a first contraction threshold at which a first portion of diaphragm muscles contract, in response to stimulating a first phrenic nerve, to draw a first desired tidal volume into lungs of a patient;
        determining a second contraction threshold at which a second portion of the diaphragm muscles contract, in response to stimulating a second phrenic nerve, to draw a second desired tidal volume into the lungs of the patient;
        generating, via at least one signal generator, a first pacing signal having a first amplitude less than the first contraction threshold;
        delivering the first pacing signal in proximity to a first phrenic nerve, thereby stiffening the first portion of the diaphragm muscles;
        generating, via the at least one signal generator, a second pacing signal having a second amplitude equal to or greater than the second contraction threshold, the second amplitude being different from the first amplitude; and
        while delivering the first pacing signal, delivering the second pacing signal in proximity to a second phrenic nerve, thereby contracting the second portion of the diaphragm muscles.

9. The ventilator system of claim 8, wherein the set of operations further comprises:

modifying at least one of the first pacing signal or the second pacing signal, based on a third desired tidal volume.

10. The ventilator system of claim 9, wherein modifying the at least one of the first pacing signal or the second pacing signal comprises changing at least one of: a frequency, a pulse duration, a pulse shape, or an amplitude.

11. The ventilator system of claim 9, wherein the set of operations further comprises:
delivering the third desired tidal volume.

12. The ventilator system of claim 8, wherein the set of operations further comprises:
modifying a first output signal based on the first threshold until a measured tidal volume is within a range of a third desired tidal volume; and
modifying a second output signal based on the second threshold until a measured tidal volume is within a range of the third desired tidal volume.

13. The ventilator system of claim 8, further comprising a ventilator chassis configured to provide positive pressure ventilation to the patient.

14. The ventilator system of claim 8, wherein the set of operations further comprises:
measuring an end-tidal carbon dioxide measurement associated with a breathing cycle; and
modifying at least one of the first pacing signal or the second pacing signal, based on the end-tidal carbon dioxide measurement.

15. A method for providing bilateral phrenic nerve pacing comprising:
generating a first pacing signal having a first amplitude;
delivering the first pacing signal in proximity to a first phrenic nerve, thereby stiffening a first portion of diaphragm muscles;
generating a second pacing signal having a second amplitude different from the first amplitude; and
while delivering the first pacing signal, delivering the second pacing signal in proximity to a second phrenic nerve, thereby contracting a second portion of the diaphragm muscles.

16. The method of claim 15, the method further comprising:
receiving a contraction threshold, wherein the diaphragm muscles contract at amplitudes above the contraction threshold and stiffen at positive amplitudes below the contraction threshold.

17. The method of claim 16, wherein the first amplitude is less than the contraction threshold and the second amplitude is greater than or equal to the contraction threshold.

18. The method of claim 16, wherein the contraction threshold includes a first contraction threshold associated with the first portion of the diaphragm muscles and a second contraction threshold associated with the second portion of the diaphragm muscles.

19. The method of claim 15, the method further comprising modifying a parameter of the first pacing signal to achieve a tidal volume, wherein the parameter is one of:
a frequency;
a pulse duration; or
a pulse shape.

20. The method of claim 15, the method further comprising:
providing positive pressure ventilation to the patient while delivering the first pacing signal and the second pacing signal.

* * * * *